(12) United States Patent
Kwon et al.

(10) Patent No.: US 8,124,767 B2
(45) Date of Patent: Feb. 28, 2012

(54) LUMINESCENCE BIOTIN-TRANSITION METAL COMPLEX CONJUGATE, AND METHOD OF AMPLIFYING SIGNAL USING THE SAME

(75) Inventors: Tae-hyuk Kwon, Seoul (KR); Jong-chul Kwon, Seoul (KR); Jong-in Hong, Seoul (KR)

(73) Assignees: Samsung Electronics Co., Ltd. (KR); Seoul National Univeristy Industry Foundation (KR)

( * ) Notice: Subject to any disclaimer, the term of this patent is extended or adjusted under 35 U.S.C. 154(b) by 450 days.

(21) Appl. No.: 12/370,353

(22) Filed: Feb. 12, 2009

(65) Prior Publication Data

US 2009/0209048 A1    Aug. 20, 2009

(30) Foreign Application Priority Data

Feb. 14, 2008   (KR) ........................ 10-2008-0013715

(51) Int. Cl.
*C07D 495/04*    (2006.01)

(52) U.S. Cl. ......................................................... 546/4

(58) Field of Classification Search .................. 546/256, 546/4
See application file for complete search history.

(56) References Cited

PUBLICATIONS

Lo et al. Inorganic Chemistry 2007, 46, 700-709.*
Stark, J., Nature, 1907, vol. 75, p. 295.*
Lo et al. Coordination Chemistry Reviews 2006, 250, 1724-1736.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Kwon, T.H et al., Highly Efficient Light-Harvesting System Based on a Phosphorescent Acceptor Coupled with Dendrimer Donors via Singlet-Singlet and Triplet-Triplet Energy Transfer, Chem. Mater., 2007, 19 (15), pp. 3673-3680.
Li, Z. et al., Novel Peptidyl α-Keto Amide Inhibitors of Calpains and Other Cysteine Proteases, J. Med. Chem., 1996, 39 (20), pp. 4089-4098.
Lo, K. K.W. et al., Bifunctional Luminescent Rhenium(I) Complexes Containing an Extended Planar Diimine Ligand and a Biotin Moiety, Organometallics, 2004, 23 (12), pp. 3062-3070.
Wang, Z.X. et al., A Novel Spectroscopic Titration Method for Determining the Dissociation Constant and Stoichiometry of Protein-Ligand complex, Anal. Biochem. 1992, 206, pp. 376-381.

* cited by examiner

*Primary Examiner* — Joseph Kosack
*Assistant Examiner* — Matthew Coughlin
(74) *Attorney, Agent, or Firm* — Cantor Colburn LLP

(57) ABSTRACT

Disclosed are a luminescence biotin-transition metal complex conjugate and a method of amplifying signals using the same. More particularly, disclosed herein are a luminescence biotin-transition metal complex conjugate comprising an energy acceptor and biotin, and optionally an energy donor and a method of amplifying signals using the biotin-transition metal complex conjugate using intramolecular energy transfer. The luminescence biotin-transition metal complex conjugate using a transition metal probe provides a phosphorescence detection system capable of improved sensitivity.

3 Claims, 14 Drawing Sheets

LUMINESCENCE BIOTIN-TRANSITION METAL COMPLEX CONJUGATE, AND METHOD OF AMPLIFYING SIGNAL USING THE SAME

CROSS-REFERENCE TO RELATED APPLICATIONS

This application claims priority to Korean Patent Application No. 10-2008-0013715, filed on Feb. 14, 2008 and all the benefits accruing therefrom under 35 U.S.C. §119, the contents of which in its entirety are hereby incorporated by reference.

BACKGROUND

1. Field

This disclosure relates to a luminescence biotin-transition metal complex conjugate and a method of amplifying signals using the same.

2. Description of the Related Art

The extremely strong binding interaction between biotin and (strept)avidin has widespread bioanalytical applications such as the detection of biomolecules, clinical diagnosis, and immunoassays. Of the many techniques for biotin-(strept) avidin assays, there has been considerable interest in transition metal complexes using phosphorescence to overcome the problems of organic fluorophores such as the strong pH dependence, low photostability, small Stokes shifts, and short lifetimes. Among the transition metal complexes using phosphorescence, Ir(III) complexes are promising candidates in various bioanalytical applications on account of their intense emission, wide range of emission energies, and high luminescence quantum yield. However, most ionic transition metal complexes developed as biological labeling reagents did not show high sensitivity upon binding to (strept)avidin. For example, the luminescence enhancement factor of previous transition metal complexes upon binding to (strept)avidin is usually in the range of about 1-3 fold. This is because the luminescence enhancement only results from the increased hydrophobicity of the surrounding environment of the bound probes, compared with the environment of the free probes.

SUMMARY

Disclosed herein is a luminescence biotin-transition metal complex conjugate

Disclosed herein too is a method of amplifying signals using the luminescence biotin-transition metal complex conjugate.

Disclosed herein too is a luminescence biotin-transition metal complex conjugate including an energy acceptor and biotin, and optionally comprising an energy donor.

Disclosed herein too is a method of amplifying signals using the biotin-transition metal complex conjugate using intramolecular energy transfer.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION

Figure 1:
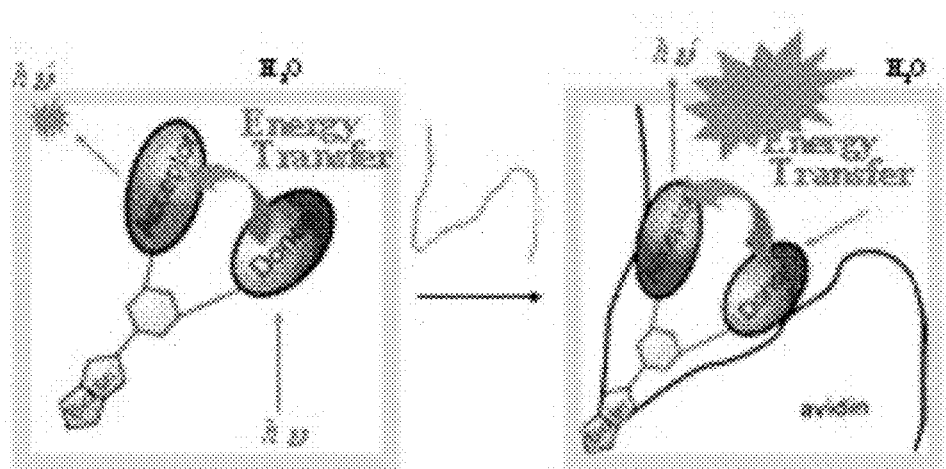
FIG. 1 is a schematic drawing illustrating a neutral tripodal probe system.

Hereinafter, the invention will be described more fully with reference to the accompanying drawings, in which exemplary embodiments of the invention are shown. Reference will now be made in detail to embodiments, examples of which are illustrated in the accompanying drawings, wherein like reference numerals refer to the like elements throughout. In this regard, the embodiments disclosed herein may have different forms and should not be construed as being limited to the descriptions set forth herein. Accordingly, the embodiments are merely described below by referring to the figures, to explain aspects of the description.

Hereinafter, a neutral tripod system for biotin-avidin assays will be described. More specifically, hereinafter a luminescence biotin-transition metal complex conjugate and a method of amplifying signals using the same according to an embodiment will be described.

In one embodiment, a luminescence biotin-transition metal complex conjugate includes an energy acceptor and biotin, and selectively an energy donor (FIG. 1). This tripodal system provides a dramatic increase in luminescence intensity due to the intramolecular energy transfer between the donor and acceptor, as well as the increased hydrophobicity of the neutral probe, upon binding to avidin. Thus, the luminescence biotin-transition metal complex conjugate may be used as a tripodal system for a biotin-avidin assay using intramolecular energy transfer luminescence enhancement.

transition metal-based probes due to intramolecular energy transition and increased hydrophobicity with the avidin-binding site. Further, the neutral Probe 1 may be used as a homogenous competitive biotin assay. In one embodiment, the biotin can be substituted with various recognition elements for various biomolecules, thereby manufacturing another biomolecular probe system.

In one embodiment, the luminescence biotin-transition metal complex conjugate the energy acceptor may be Iridium (III) bis[(4,6-difluorophenyl)-pyridinato-N,C²']picolinate ("Flrpic"), represented by Formula 3 below.

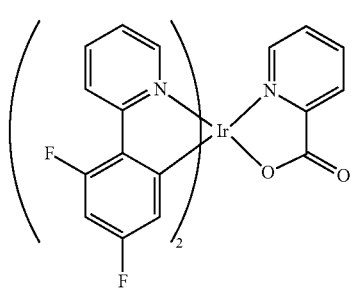

In one embodiment of the luminescence biotin-transition metal complex conjugate, the energy acceptor and the biotin-transition metal may form a transition metal probe represented by Formula 2 below, which is an electrically neutral control probe without an energy donor.

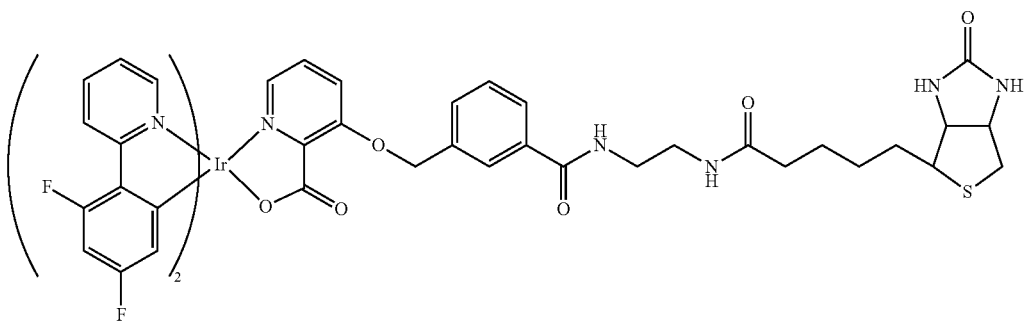

In another embodiment, the luminescence biotin-transition metal complex conjugate includes biotin, Flrpic as an energy acceptor, and mCP as an energy donor.

In one embodiment, the biotin-transition metal complex conjugate includes the energy acceptor, the energy donor, and biotin combined with one another via covalent bonds. Alternatively, the energy acceptor, the energy donor, and/or biotin may combine with one another directly or using a linker. Thus, the energy acceptor, the energy donor, and/or biotin are not in a simple mixture state.

The biotin-transition metal complex conjugate is a highly sensitive phosphorescence detection system which may increase sensitivity of the existing biotin-avidin assay. Neutral systems can offer a more hydrophobic environment than ionic probes. Therefore, these neutral systems show a high binding affinity and reduce the nonspecific interaction that can exist between the protein surface and ionic transition metal probe. Thus, the neutral tripod system for the biotin-avidin assay provides improved sensitivity over traditional In one embodiment of the luminescence biotin-transition metal complex conjugate, the energy donor may be N,N'-dicarbazolyl-3,5-benzene ("mCP"), represented by Formula 4 below.

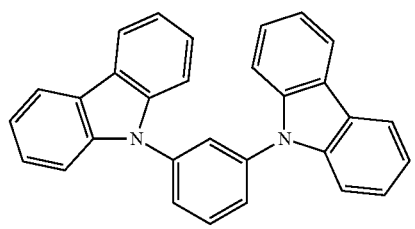

In an exemplary embodiment of the luminescence biotin-transition metal complex conjugate the energy acceptor, the energy donor, and the biotin-transition metal may form a transition metal probe represented by Formula 1 below.

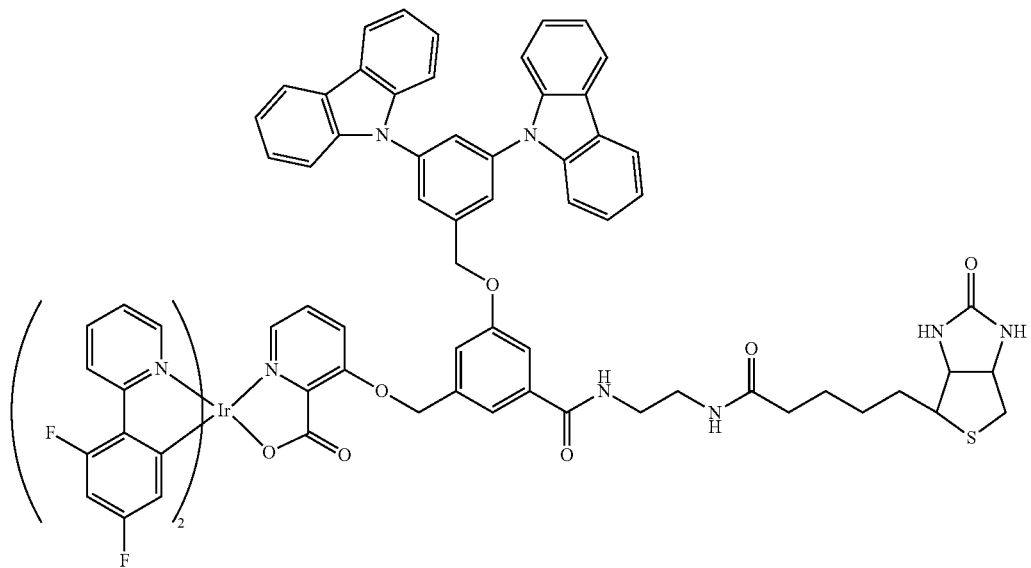

In an exemplary embodiment, the luminescence biotin-transition metal complex conjugate may be a probe represented by Formula 1 or 2 above (hereinafter, a probe represented by Formula 1 is referred to as "Probe 1" and a probe represented by Formula 2 is referred to as "Probe 2"). In the transition metal probe represented by Formula 1 or 2, a singlet-singlet energy transfer or a triplet-triplet energy transfer may occur from the energy donor (mCP) to the energy acceptor (Flrpic) in overlapped regions metal-to-ligand charge transfer ("$^1$MLCT") and ligand-centered ("$^3$LC") regions) between an emission spectrum of the energy donor ("mCP" unit) and an absorption spectrum of the energy acceptor ("Firpic") at 350 nm.

The luminescence of the transition metal probes represented by Formula 1 or 2 may occur at both $^1$MLCT(dπ(Ir)→π*(N—O)) region and $^3$LC region in the energy acceptor moiety (Flrpic) and the transition metal probes have an emission spectrum ($\lambda_{max}$=472 nm) similar to that of Flrpic.

As shown in FIG. 1, a luminescence biotin-transition metal complex conjugate, according to one embodiment, may provide a tripodal system including an energy acceptor, an energy donor, and biotin, used for a biotin-avidin assay.

The tripodal system disclosed herein may provide not only an increase in hydrophobicity of a neutral probe but also provide a rapid increase in the emission intensity caused by an intramolecular energy transfer between the energy donor and the energy acceptor while the tripodal system is binding to avidin. The luminescence biotin-transition metal complex conjugate uses an intramolecular energy transfer to increase the emission efficiency.

Neutral systems may offer a more hydrophobic environment than ionic probes. Thus, they are expected to exhibit a high binding affinity and reduce the nonspecific interaction between the surface of proteins and ionic transition metal probes.

As demonstrated by Formula 3, Iridium(III) bis[(4,6-difluorophenyl)-pyridinato-N,C$^{2'}$]picolinate ("Firpic"), which is well known sky blue dopant in organic light emitting devices ("OLEDs"), may be selected as an energy acceptor on account of its high quantum efficiency. N,N'-dicarbazolyl-3,5-benzene ("mCP") may be selected as an energy donor that demonstrates higher singlet and triplet energies than the energy acceptor.

As demonstrated by Formula 2, a control probe (Probe 2) without an energy donor, which has a similar structure to that of previous transition metal probes but is electrically neutral, may also be prepared. The luminescence of Probes 1 and 2 may result from both $^1$MLCT(dπ(Ir)→π*(N—O)) transition and $^3$LC transition in the energy acceptor moiety ("Firpic"), and have similar emission spectrum ($\lambda$max=472 nm) to the energy acceptor ("Firpic"). There is a good overlap between the emission spectrum of the energy donor ("mCP" unit) and the absorption spectrum of the energy acceptor ("Firpic") over 350 nm at $^1$MLCT and $^3$LC regions, which ensures singlet-singlet energy transfer from the energy donor ("mCP") to the energy acceptor ("Firpic"). The singlet-singlet intramolecular energy transfer in Probe 1 from the energy donor (mCP) to the energy acceptor ("Firpic") exhibits a high efficiency of 92% via the transient PL method. Furthermore, the distance between the energy donor and the energy acceptor (~15 Å, under the assumption that all the bonds are linked through a trans geometry) in the optimized geometric structure of Probe 1 and density functional theory ("DFT") calculations suggest that the effective triplet-triplet energy transfer between the energy donor and the energy acceptor may also occur. The triplet-triplet energy transfer efficiency of Probe 1 was estimated to be 99% via the transient PL method.

Hereinafter, a luminescence biotin-transition metal complex conjugate including an energy acceptor, an energy donor, and biotin for biotin-avidin assay according to an embodiment will be described in more detail with reference to accompanying drawings and experimental results.

Figure 13A:
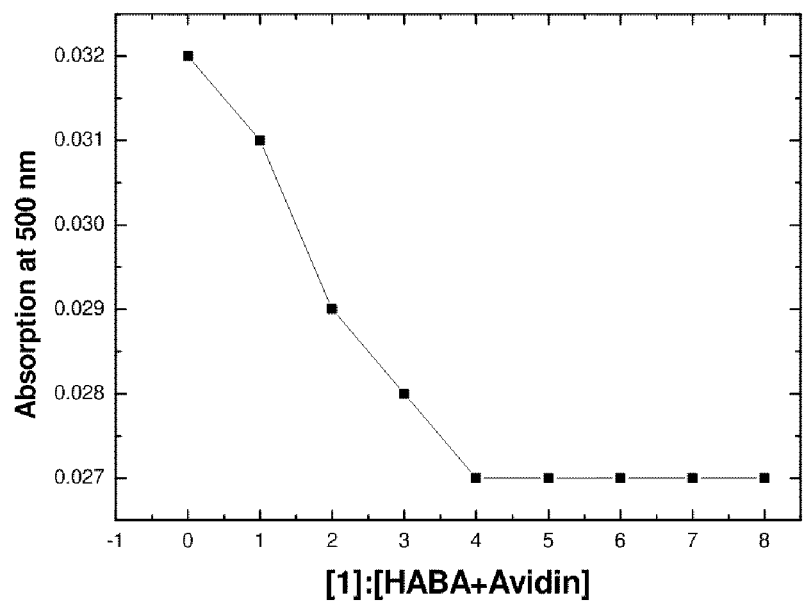
FIGS. 13A and 13B are graphs illustrating absorption changes for the titrations of avidin-HABA complex with Probe 1 (13A) and with Probe 2 (13B)
Figure 13B:
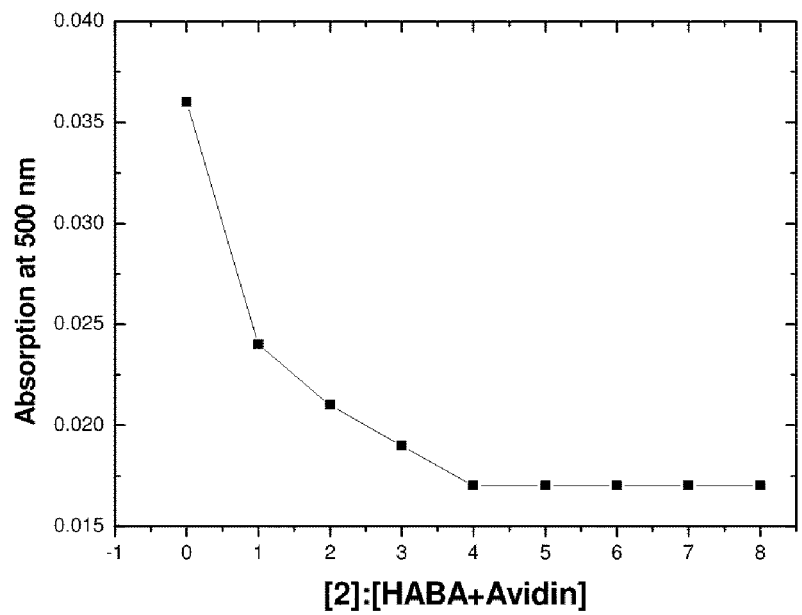
Figure 14:
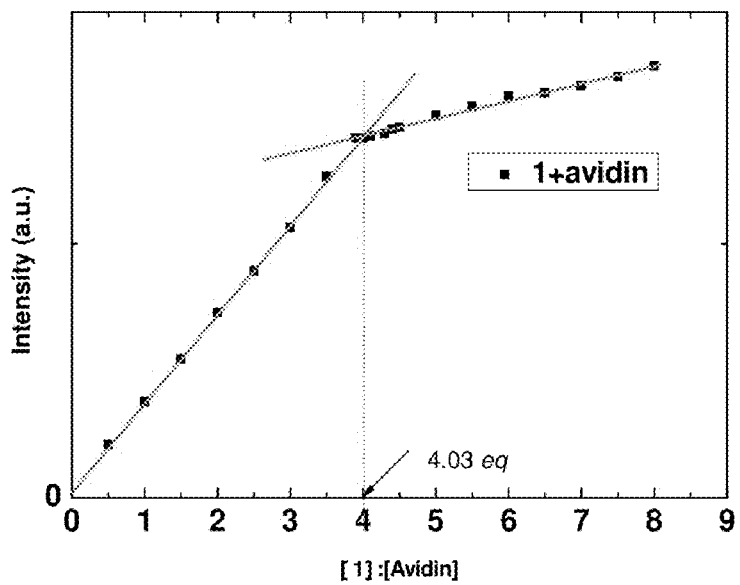
FIG. 14 is a graph illustrating determining $K_d$ value of Probe 1 based on luminescence intensity changes for the titration of avidin (1.66 M) with Probe 1.
Figure 15:
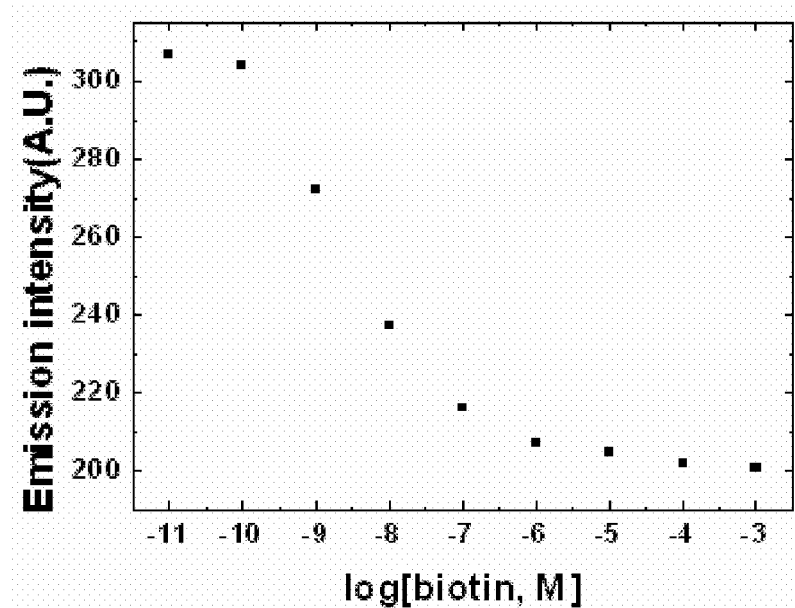
FIG. 15 is a graph illustrating a homogeneous biotin competitive assay using Probe 1 (6.64 µM) and avidin (1.66 µM), wherein the emission intensity is measured at 472 nm.

The avidin-binding properties of Probes 1 and 2 are investigated using the standard 4,4'-hydroxyazobenzene-2-carboxylic acid ("HABA") assay, which are based on the competition between biotin and HABA for binding to avidin, and luminescence titration experiments. As shown in FIGS. 13A and 13B, the addition of Probe 1 or 2 into a mixture of HABA (1 mM) and avidin (1.66 μM) results in a decrease in absorbance at 500 nm. This shows that the bound HABA molecules are replaced by Probes 1 and 2 with the same stoichiometry as free biotin.

Figure 2:
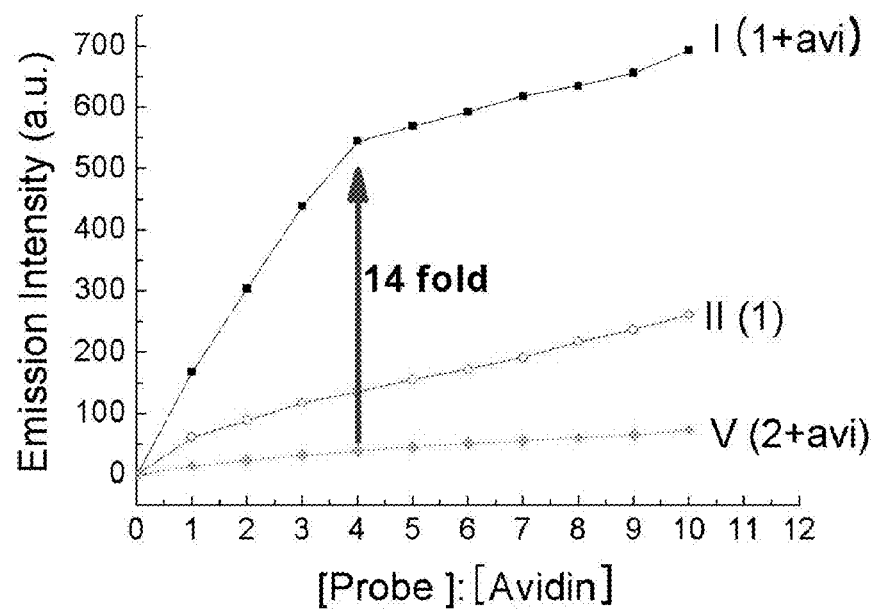
FIG. 2 is a graph illustrating the emission intensity of Probe 1-avidin (1.66 µM) complex at the excitation at 380 nm (I), emission intensity of Probe 1 in a buffer A solution at the excitation at 310 nm (II), emission intensity of Probe 2-avidin (1.66 µM) complex at the excitation at 310 nm (V).
Figure 12:
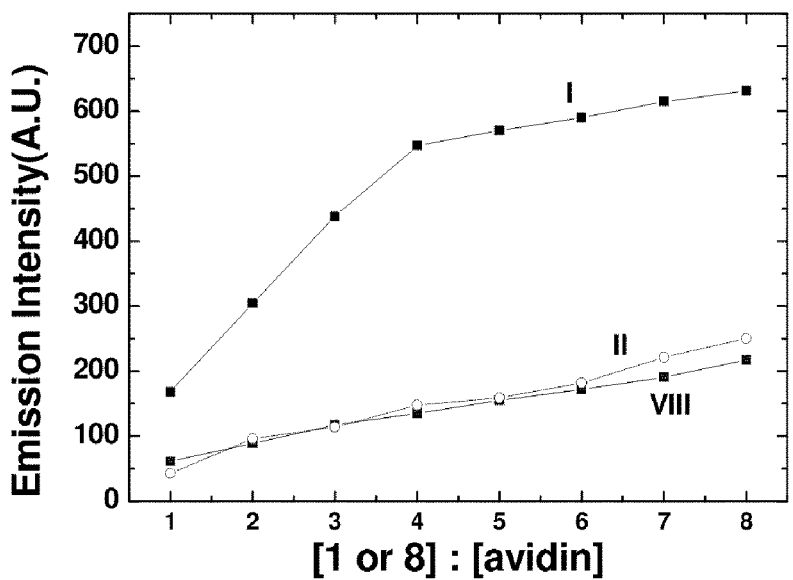
FIG. 12 is a graph illustrating luminescence intensity changes for the titration of avidin with Probe 1 (I), Probe 1 (II), and the titration of avidin with Compound 8 (VIII), in a buffer solution at 310 nm excitation.

As shown in FIGS. 1 and 2, upon binding to avidin, the neutral tripod Probe 1 showed a dramatic increase in emission intensity when excited at the energy donor absorption peak (310 nm), rather than at the MLCT region of the energy acceptor (380 nm). Luminescence titration using Probe 1 exhibits a turning point at 4 equivalents of Probe 1 due to strong interaction of the biotin moiety with the four binding sites of avidin (due to the solubility problem of the Probes 1 and 2 in aqueous solvent, $H_2O$:DMSO (9:1, v/v) was used in all the titrations) ((I), (FIG. 2)). Luminescence titration using Probe 1 also shows a remarkable increase in emission intensity (I) (about 14-fold) at Probe 1:avidin=4:1, when excited at the energy donor (mCP unit) absorption peak (310 nm), compared with that of Probe 2 (V) without an energy donor upon 4:1 binding with avidin when excited at the MLCT region (380 nm) (FIG. 2). Furthermore, the emission intensity of Probe 1-avidin complex dramatically increases with increasing concentration of Probe 1 until it fully binds to avidin, and about 4-fold higher than that of Probe 1 itself (II) when excited at 310 nm. At over 4 equivalents, the slope of the Probe 1-avidin complex (I) becomes similar to that of Probe 1 (II) without avidin. This indicates that the increase in emission with more than 4 equivalents of Probe 1 just reflects the increase in the probe concentration. Therefore, a nonspecific interaction between the free probes and the protein surface may be excluded. Compound 8 without a biotin moiety showed no increase in emission intensity in the presence of avidin (FIG. 12).

Figure 7:
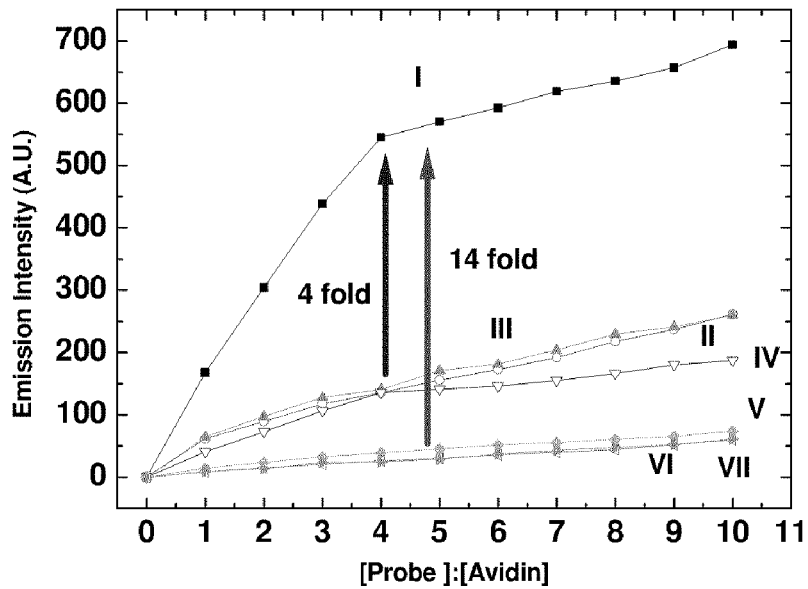
FIG. 7 is a graph illustrating the luminescence intensity change for the titration of avidin with Probe 1 at 310 nm excitation (I), Probe 2 at 310 nm excitation (II), the titration avidin+excess biotin with Probe 1 at 310 nm excitation (III), the titration avidin with Probe 1 at 380 nm excitation (IV), the titration of avidin with Probe 1 at 380 nm excitation (V), Probe 2 at 380 nm excitation (VI), and the titration of avidin+ excess biotin with Probe 2 at 380 nm excitation (VII), wherein all of the luminescence titration are conducted in buffer solution.

In contrast, as show in FIG. 7, the luminescence titration with Probe 2 shows that the emission intensity of the Probe 2-avidin complex (V) is about 1.6 times that of Probe 2 in the absence of avidin (VI). The emission intensity of Probe 1 (II) excited at 310 nm was significantly larger than that of Probe 2 (VI) excited at 380 nm, and increased with increasing concentration of the probe due to intramolecular energy transfer (FIG. 7). This indicates that intramolecular energy transfer may be an effective method for increasing the sensitivity ($\Phi_{ET}$>74%, in avidin+Probe 1). In addition, the emission intensity of Probe 1 (IV) in the presence of avidin, excited at 380 nm (MLCT region of Flrpic), was much lower than when excited at 310 nm ((I), (FIG. 7)). The lifetime of Probes 1 and 2 in the presence of avidin was elongated about 2.0 and 1.9 fold, respectively, due to the hydrophobic environment of the biotin-binding sites of avidin as shown in Table 1 below. This is supported by the fact that the lifetimes of the Probes 1 and 2 decrease with increasing solvent polarity (Table 1). The addition of excess biotin to a 1:4 mixture of avidin and Probe 1 (or 2) restored the original lifetime of Probe 1 (or 2) before complexation. Therefore, the increase in emission intensity results from intramolecular energy transfer and the hydrophobicity associated with the binding sites of avidin. Therefore, this tripod system may be used effectively used for labeling of biomolecules.

Figure 3:
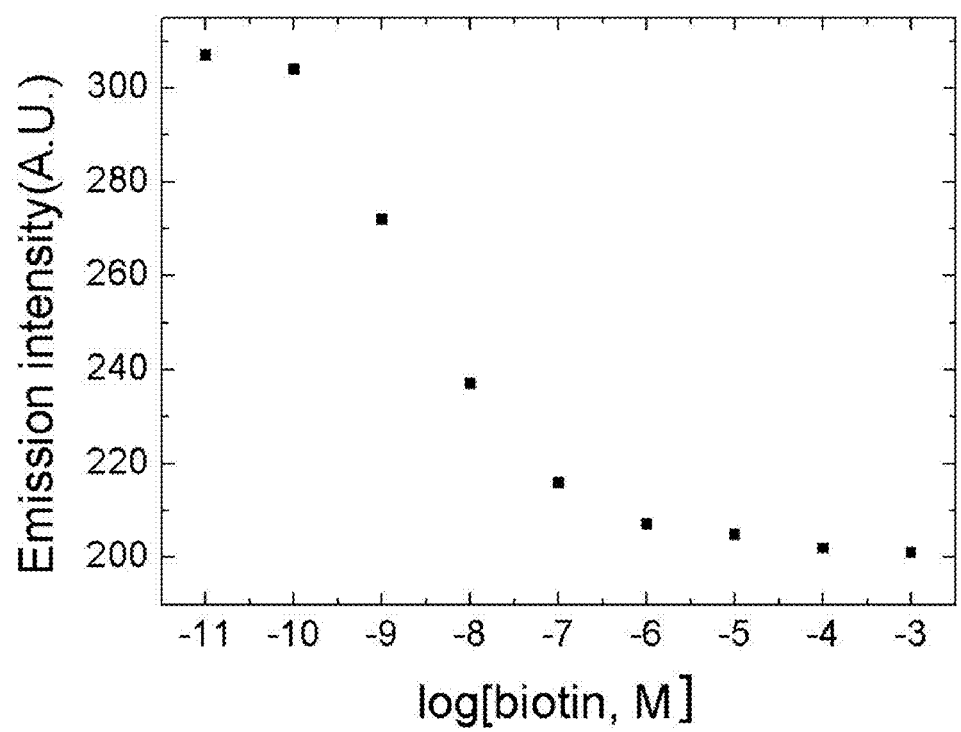
FIG. 3 is a graph illustrating the results of a homogeneous biotin competitive assay using avidin (1.66 µM) and Probe 1 (6.64 µM), wherein the emission intensity is measured at 472 nm.
Figure 4A:
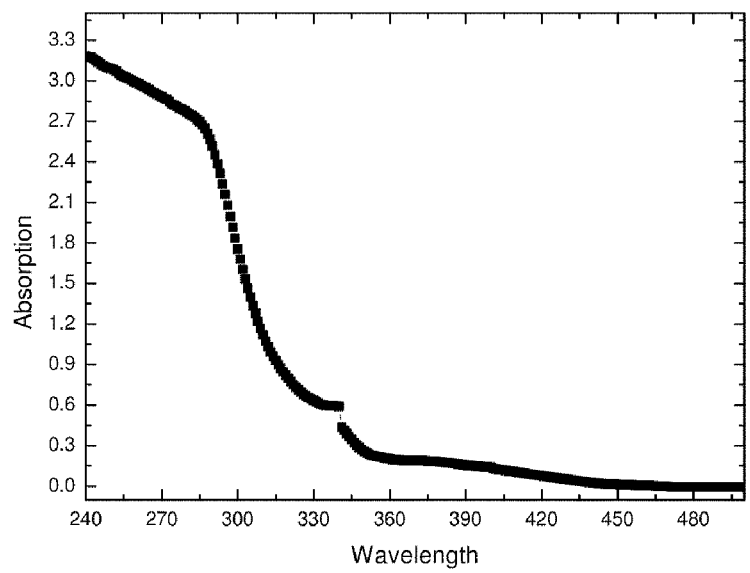
FIGS. 4A and 4B are graphs illustrating UV spectra of Probe 1 (4A) and Probe 2 (4B) in $CH_3CN$ (0.02 mM)
Figure 4B:
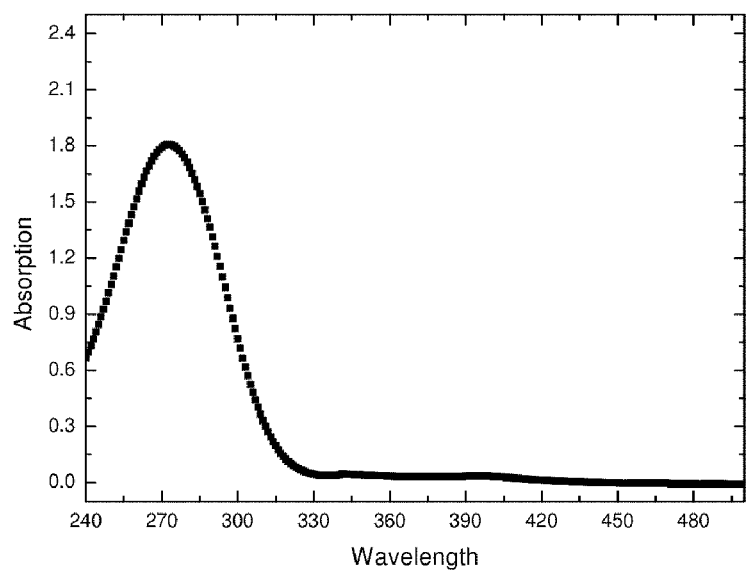

As shown in FIG. 3, a homogenous competitive biotin assay was carried out by adding free biotin in a range of about $10^{-11}$ to about $10^{-3}$ M to a mixture of Probe 1 (6.64 μM) and avidin (1.66 μM) in buffer A solution. After 1 hour of incubation, the emission intensity of Probe 1 decreases gradually according to the concentration of free biotin because the binding of free biotin to avidin ($K_d$=ca. $10^{-15}$ M) is much stronger than that of Probe 1. Due to the high emission intensity of Probe 1-avidin complex, the linear range for the detection of the free biotin analyte is increased greatly to $10^{-6.5}$~$10^{-10.5}$ M. Compared with ionic transition metal probes, the detection limit of the current system is higher by two or three orders of magnitude.

In one embodiment, the invention provides a method of amplifying signals using the biotin-transition metal complex conjugate. For the method of amplifying signals the biotin-transition metal complex conjugate may significantly increase emission intensity upon biding to avidin using a neutral tripod iridium complex binding to avidin.

EXAMPLES

Probe 1 is synthesized through Scheme S2, and Probe 2 is synthesized through Scheme S3. Intensities of binding signals between biotin and avidin caused by intramolecular energy transfer of Probes 1 and 2 are measured using PL spectrum assay of Probes 1 and 2, luminescence titration, HABA assay, $K_d$ determination, competitive biotin assay, energy transfer efficiency in 2-MeTHF (steady-state PL, transient PL, Tables 2 and 3), and energy transfer efficiency in a buffer solution (Table 4) (FIGS. 5-18).

Example 1

Buffer and Reagent

Buffer A solution contained 100 mM NaCl, 50 mM $NaH_2PO_4$, and 1 mM EDTA, and was adjusted to pH 7.5 using NaOH. 10% DMSO in $H_2O$ was used in order to increase solubility of Probes 1 and 2 in an aqueous solution. Avidin and 4,4'-hydroxyazobenzene-2-carboxylic acid ("HABA") were purchased from Aldrich. D-Biotin was purchased from TCI company. N,N'-diisopropylethylamine ("DIPEA"), 1-hydroxybenzotriazole ("HOBt"), and benzotriazol-1-yl-oxytripyrrolidinophosphonium hexafluorophosphate ("PyBOP") were purchased from Aldrich. Analytic thin-layer chromatography was performed using Kieselgel 60F-254 plates from Merck. Column chromatography was carried out on Merck silica gel 60 (70-230 mesh). All solvents and reagents are commercially available and used without further purification unless otherwise noted.

Example 2

Instruments $^1$H and $^{13}$C NMR spectra were recorded using Advance 300 or 500 MHz Bruker spectrometer in $CDCl_3$ and DMSO-$d_6$. $^1$H NMR chemical shifts in DMSO-$d_6$ were reference to $CH_3SOCH_3$ (2.50 ppm), and $^{13}$C NMR chemical shifts in DMSO-$d_6$ were reported relative to $CH_3SOCH_3$ (38 ppm). UV-Vis spectra were recorded on a Beckman DU650 spectrophotometer. Mass spectra were obtained using a MALDI-TOF Mass Spectrometry from Bruker. Phosphorescence lifetime data were obtained using FRET MASTER-1 from PTI. Fluorescence spectra were recorded on Jasco FP-7500 spectrophotometer.

TABLE 1

Photophysical properties and lifetime of Probes 1 and 2 at 298 K

| | medium | $\lambda_{max}$/nm ($\Phi_{PL}{}^b$) | T (μs)$^c$ | T (μs)$^d$ | T (μs)$^e$ |
|---|---|---|---|---|---|
| Probe 1 | $CH_2Cl_2$ | 472, 519 (0.28) | 1.01 | | |
| | $CH_3CN$ | 473, 498 (0.14) | 0.49 | | |
| | $H_2O^a$ | 474, 505 (0.01) | 0.28 | 0.56 | 0.28 |
| Probe 2 | $CH_2Cl_2$ | 469, 496 (0.10) | 0.92 | | |
| | $CH_3CN$ | 472, 493 (0.03) | 0.45 | | |
| | $H_2O^a$ | 463, 501 (0.01) | 0.26 | 0.49 | 0.25 |

$^a$pH 7.5, buffer A solution ($H_2O$/DMSO = 9:1). Quantum yield was measured using Flrpic ($\Phi_{PL}$ = 0.42) as a reference.
$^c$[1] = [2] = 6.64 μM, [avidin] = 0 μM.
$^d$[1] = [2] = 6.64 μM, [avidin] = 1.66 μM.
$^e$[1] = [2] = 6.64 μM, [avidin] = 1.66 μM, [biotin] = 166 μM.

Example 3
Synthesis
Scheme S1: Synthesis of Compound 3
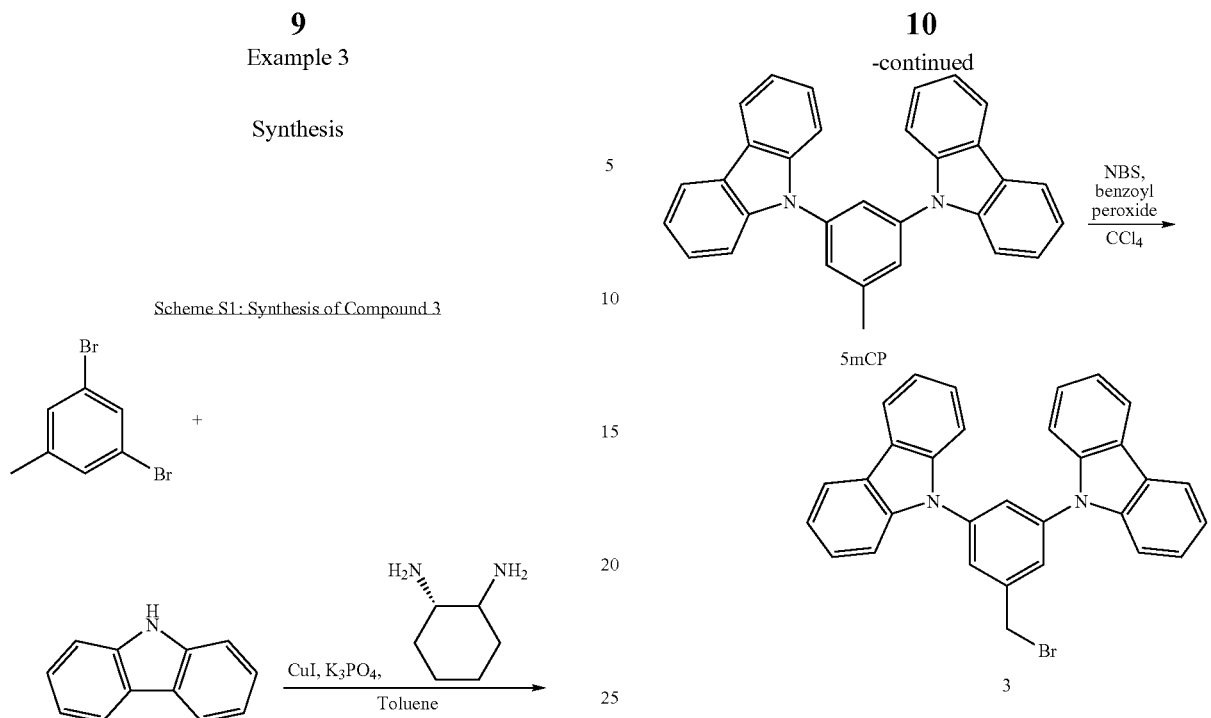
5 mCP-Br (3) was prepared according to the process disclosed in Kwon, T. -H.; Kim, M. K.; Kwon, J.; Lee, C. L.; Kim, J. J.; Park, S. J.; Shin, D. Y.; Hong, J. I., *Chem. Mater.* 2007, 19, 3673.
Scheme S2: Synthesis of Probe 1
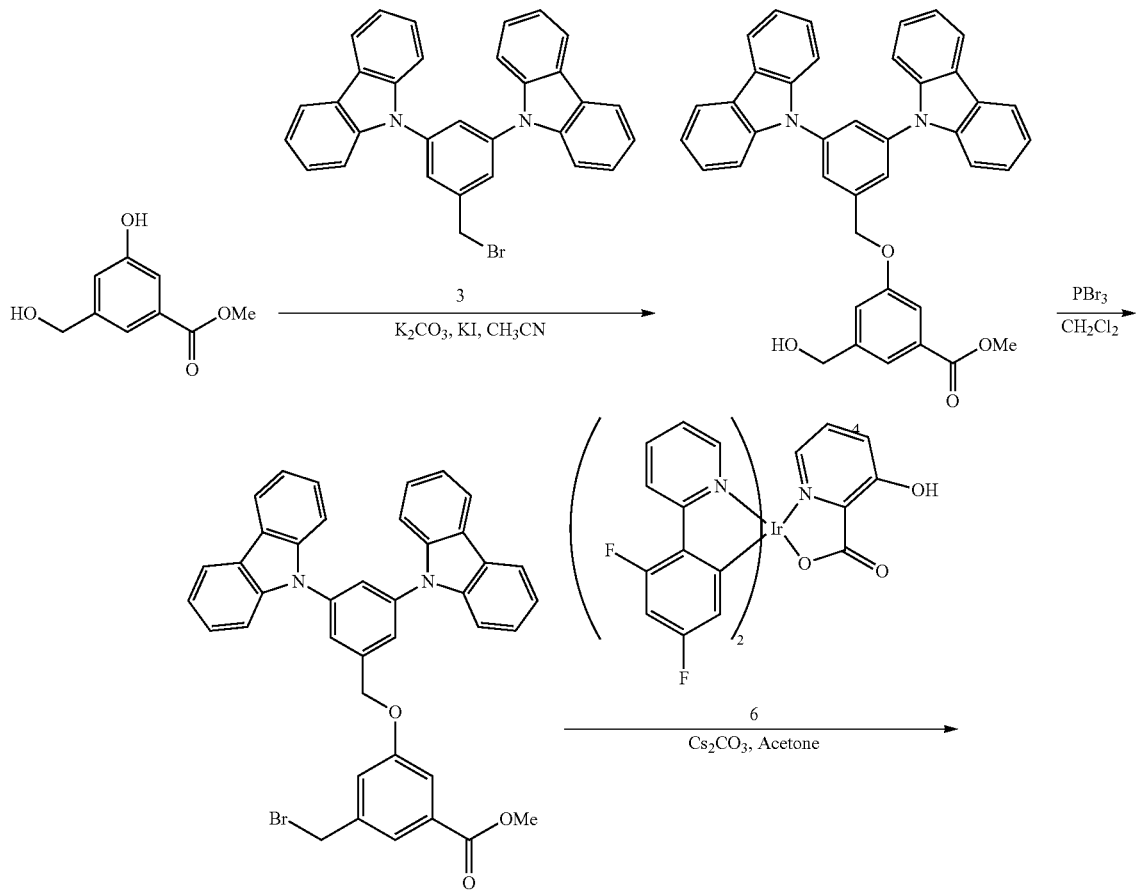

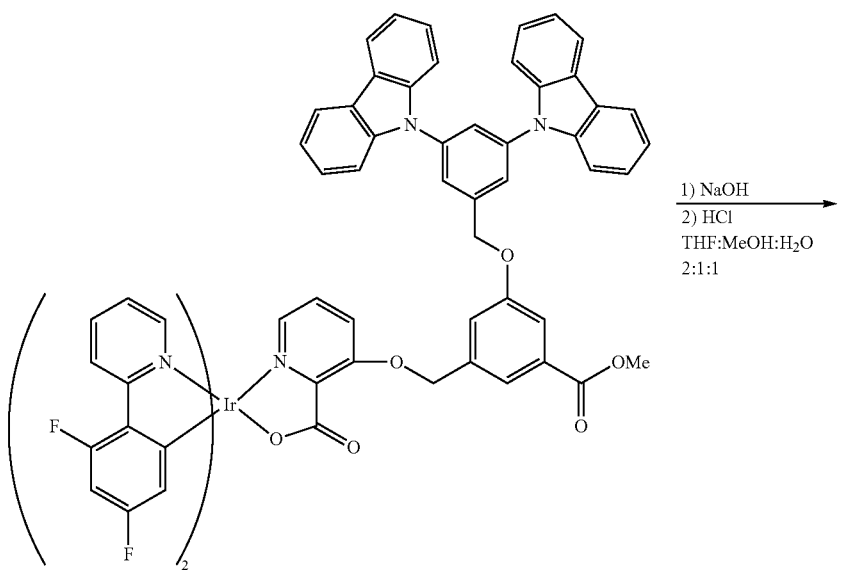
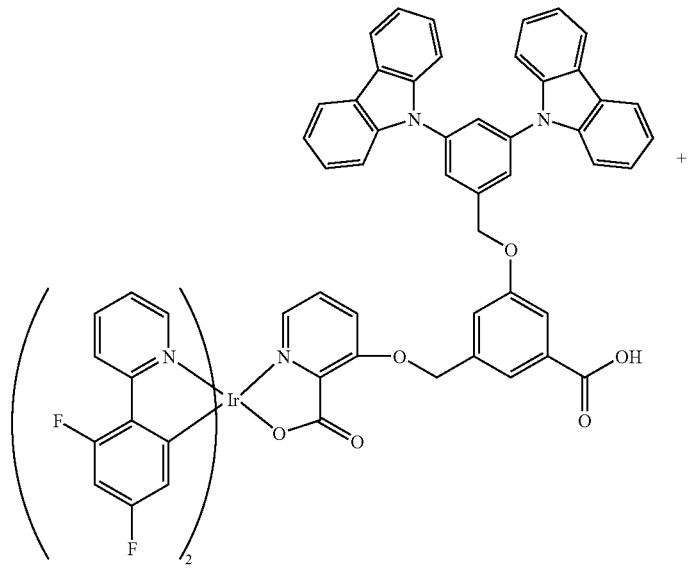
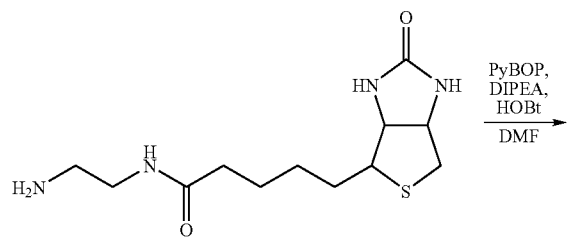

-continued

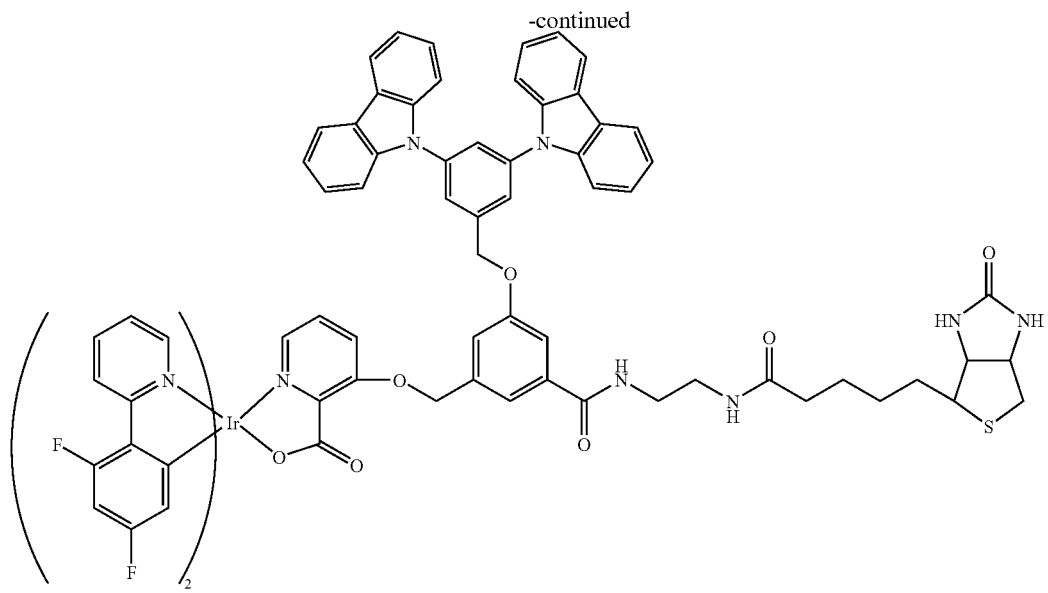

Flrpic-OH (Compound 6) was prepared according to the process disclosed in Kwon, T.-H.; Kim, M. K.; Kwon, J.; Lee, C. -L; Kim, J. -J.; Park, S.-J.; Shin, D. Y.; Hong, J.-I. Chem. Mater. 2007, 19, 3673. Biotinylated amine (9) was prepared according to the process disclosed in Li, Z.; Ortega-Vilain, A.-C.; Patil, G. S.; Chu, D. L.; Foreman, J. E.; Eveleth, D. D.; Powers, J. C., J. Med. Chem. 1996, 39, 4089-4098.

Synthesis of Compound 4: A mixture including 3-hydroxy-5-hydroxymethylbenzoic acid methyl ester (400 mg, 2.19 mmol), 5 mCP-Br (Compound 3) (1.10 g, 2.19 mmol), $K_2CO_3$ (908 mg, 6.57 mmol), and KI (363 mg, 2.19 mmol) was refluxed in acetonitrile for 24 hours. After cooling to room temperature, the solvent was evaporated in vacuum, and the resulting residue was dissolved in ethyl acetate. The organic phase was washed with water and brine, and dried over $Na_2SO_4$. All the volatiles were removed to give a crude (unprocessed) product, which was applied to column chromatography on silica gel, eluting with ethyl acetate and hexane (1:3, v/v) to obtain the desired product (800 mg, yield: 60.6%). The results of the column chromatography for Compound 4 are as follows.

$^1$H NMR (300 MHz, DMSO-$d_6$): δ (ppm) 8.26 (d, 9 Hz, 4H), 7.87 (s, 2H), 7.81 (s, 1H), 7.61 (s, 1H), 7.55 (s, 1H), 7.54 (d, 6 Hz, 4H), 7.45 (t, 15 Hz, 4H), 7.34 (s, 1H), 7.31 (t, 15 Hz, 4H), 5.54 (s, 2H), 4.56 (s, 2H), 3.84 (s, 3H). $^{13}$C NMR (125 MHz, DMSO-$d_6$): δ (ppm) 166.11, 157.92, 145.23, 141.37, 139.87, 138.56, 130.81, 126.42, 124.41, 123.41, 122.97, 120.60, 120.41, 119.80, 118.23, 113.43, 109.72, 68.36, 62.18, 52.20. MALDI-TOF: calculated for $C_{40}H_{30}N_2O_4$ [M]$^+$ 602.22, measured: [M]$^+$ 602.37.

Synthesis of Compound 5: A mixture including Compound 4 (800 mg, 1.33 mmol) and PBr$_3$ (719 mg, 2.66 mmol) was stirred in methylene chloride at 0° C. for 5 hours. After completing the reaction, methanol was added to quench the residual PBr$_3$. The solvent was evaporated in vacuum, and the residue was dissolved in methylene chloride. The organic phase was washed with water and dried over $Na_2SO_4$. The solvent was evaporated to obtain the crude product, which was applied to column chromatography on silica gel, eluting with methylene chloride and hexane (1:1, v/v) to obtain the desired product (653 mg, yield: 73.7%). The results of the column chromatography for Compound 5 are as follows.

$^1$H NMR (300 MHz, CDCl$_3$): δ (ppm) 8.18 (d, 9 Hz, 4H), 7.81 (s, 1H), 7.80 (s, 2H), 7.75 (s, 1H), 7.66 (s, 1H), 7.55 (s, 1H), 7.48 (t, 6 Hz, 4H), 7.46 (t, 6 Hz, 4H), 7.36 (t, 9 Hz, 4H), 5.39 (s, 2H), 4.50 (s, 2H), 3.94 (s, 3H). $^{13}$C NMR (125 MHz, DMSO-$d_6$): δ (ppm) 166.10, 158.53, 158.03, 145.23, 140.81, 139.76, 138.59, 131.43, 126.43, 124.27, 123.69, 122.96, 121.11, 120.41, 118.23, 115.11, 109.72, 68.49, 52.38, 33.16. MALDI-TOF: calculated for $C_{40}H_{29}BrN_2O_3$ [M]$^+$ 664.14, measured: [M]$^+$ 664.35.

Synthesis of Compound 7: A mixture including Compound 5 (200 mg, 0.232 mmol), Flrpic-OH (Compound 6) (170 mg, 0.232 mmol), and Cs$_2$CO$_3$ (226 mg, 0.694 mmol) was refluxed in acetone for 24 hours. After cooling to room temperature, the solvent was evaporated in vacuum, and dissolved in methylene chloride. The organic phase was washed with water and brine, and dried over $Na_2SO_4$. The solvent was evaporated to obtain the crude product, which was applied to column chromatography on silica gel, eluting with ethyl acetate and hexane (1:1, v/v) to obtain the desired product (90 mg, yield: 30%). The results of the column chromatography for Compound 7 are as follows.

$^1$H NMR (300 MHz, DMSO-$d_6$): δ (ppm) 8.56 (d, 6 Hz, 1H), 8.24 (d, 15 Hz, 4H), 8.20 (s, 1H), 8.02 (q, 9 Hz, 2H), 7.93 (d, 9 Hz, 2H), 7.87 (s, 1H), 7.86 (s, 2H), 7.78 (d, 6 Hz, 2H), 7.64 (d, 6 Hz, 1H), 7.56 (s, 1H), 7.55 (d, 9 Hz, 4H), 7.42 (t, 6 Hz, 4H), 7.38 (s, 2H), 7.35 (s, 2H), 7.32 (t, 12 Hz, 4H), 6.79 (q, 12 Hz, 2H), 5.57 (d, 3 Hz, 1H), 5.46 (s, 2H), 5.44 (d, 3 Hz, 1H), 5.38 (s, 2H), 3.85 (s, 3H). $^{13}$C NMR (125 MHz, DMSO-$d_6$): δ (ppm) 170.06, 165.86, 163.53, 162.95, 158.25, 157.82, 153.44, 148.91, 147.97, 141.17, 141.00, 139.86, 139.34, 139.26, 139.07, 138.57, 138.35, 131.12, 130.20, 127.86, 126.44, 125.22, 124.27, 123.90, 123.47, 122.95, 122.76, 120.56, 120.35, 120.15, 118.81, 114.39, 113.65, 109.77, 69.22, 68.42, 52.30. MALDI-TOF: calculated for $C_{68}H_{44}F_4IrN_5O_6$ [M]$^+$ 1295.29, measured: [M]$^+$ 1295.79.

Synthesis of Compound 8: To a solution of Compound 7 (66 mg, 0.051 mmol) in THF:MeOH:H$_2$O (10 ml:5 ml:5 ml) was added 1 M NaOH solution. After stirring overnight at room temperature, the reaction mixture was acidified using 1 M HCl solution. The reaction mixture was filtered to obtain a yellow solid (50 mg, yield: 76.5%). The results of the column chromatography for Compound 8 are as follows.

$^1$H NMR (300 MHz, DMSO-$d_6$): δ (ppm) 8.56 (d, 6 Hz, 1H), 8.27 (s, 1H), 8.24 (d, 6 Hz, 4H), 8.20 (s, 2H), 8.00 (d, 12 Hz, 1H), 7.88 (d, 9 Hz, 1H), 7.85 (d, 3 Hz, 2H), 7.84 (d, 6 Hz, 2H), 7.78 (s, 1H), 7.73 (s, 1H), 7.64 (d, 6 Hz, 1H), 7.52 (d, 6 Hz, 4H), 7.38 (t, 18 Hz, 4H), 7.35 (s, 2H), 7.33 (s, 2H), 7.27 (t, 15 Hz, 4H), 6.78 (q, 12 Hz, 2H), 5.67 (d, 9 Hz, 1H), 5.56 (s, 2H), 5.45 (d, 9 Hz, 1H), 5.37 (s, 2H). $^{13}$C NMR (125 MHz, DMSO-$d_6$): δ (ppm) 170.04, 166.92, 163.52, 162.95, 158.64, 157.84, 154.41, 153.37, 148.90, 147.96, 141.27, 140.96, 139.84, 139.32, 139.24, 138.77, 138.35, 132.36, 130.16, 128.05, 126.43, 125.23, 124.21, 123.89, 123.41, 122.94, 122.61, 120.54, 120.33, 118.51, 114.50, 113.63, 109.76, 97.66, 69.30, 68.33. MALDI-TOF: calculated for $C_{67}H_{42}F_4IrN_5O_6$ [M]+1281.27, measured: [M]$^+$ 1281.72.

Synthesis of Compound 1: A mixture of Compound 8 (30 mg, 0.023 mmol), DIPEA (14.8 mg, 0.0155 mmol), PyBOP (35.9 mg, 0.069 mmol), and HOBt (6.21 mg, 0.046 mmol) was stirred in DMF for 1 hour, and biotinylated amine (Compound 9) (7.69 mg, 0.023 mmol) was added thereto. After stirring the mixture at room temperature for 12 hours, the solvent was evaporated under reduced pressure, and the residue was dissolved in methylene chloride. The solvent was evaporated to obtain the crude product, which was applied to column chromatography on silica gel, eluting with methylene chloride and methanol (50:1, v/v) to obtain the desired product (10 mg, yield: 27.7%). The results of the column chromatography for Compound 1 are as follows.

$^1$H NMR (300 MHz, DMSO-$d_6$): δ (ppm) 8.55 (d, 6 Hz, 1H), 8.43 (d, 6 Hz, 1H), 8.24 (d, 6 Hz, 4H), 8.20 (s, 1H), 8.01 (t, 9 Hz, 2H), 7.90 (d, 9 Hz, 2H), 7.84 (s, 2H), 7.80 (s, 2H), 7.63 (d, 6 Hz, 2H), 7.54 (t, 15 Hz, 4H), 7.52 (s, 2H), 7.41 (t, 18 Hz, 4H), 7.38 (s, 1H), 7.33 (d, 6 Hz, 2H), 7.27 (t, 15 Hz, 4H), 7.24 (s, 1H), 6.81 (q, 21 Hz, 2H), 6.32 (d, 15 Hz, 2H), 5.66 (d, 6 Hz, 1H), 5.54 (s, 2H), 5.45 (d, 9 Hz, 1H), 5.35 (s, 2H), 4.24 (d, 6 Hz, 2H), 4.05 (d, 6 Hz, 2H), 3.21 (d, 6 Hz, 2H), 3.00 (d, 6 Hz, 2H), 2.73 (s, 2H), 2.00 (m, 6 Hz, 2H), 1.42 (m, 15 Hz, 4H), 0.86 (d, 9 Hz, 1H). $^{13}$C NMR (125 MHz, DMSO-$d_6$): δ (ppm) 172.36, 171.10, 170.18, 166.00, 165.81, 164.00, 163.00, 162.65, 161.00, 159.00, 158.12, 157.91, 154.00, 153.00, 148.00, 147.95, 141.33, 139.87, 139.27, 138.57, 138.39, 138.30, 136.05, 130.23, 126.46, 125.31, 124.23, 123.46, 122.94, 120.55, 120.34, 118.44, 113.63, 113.11, 109.79, 78.00, 77.80, 65.10, 60.94, 59.14, 55.33, 40.34, 40.06, 37.67, 35.15, 28.10, 27.97, 25.17. MALDI-TOF: calculated for $C_{80}H_{66}F_4IrN_9O_7S$ [M]$^+$ 1565.4400, measured: [M+Na]$^+$ 1588.099. HR-MS: 1565.4378.

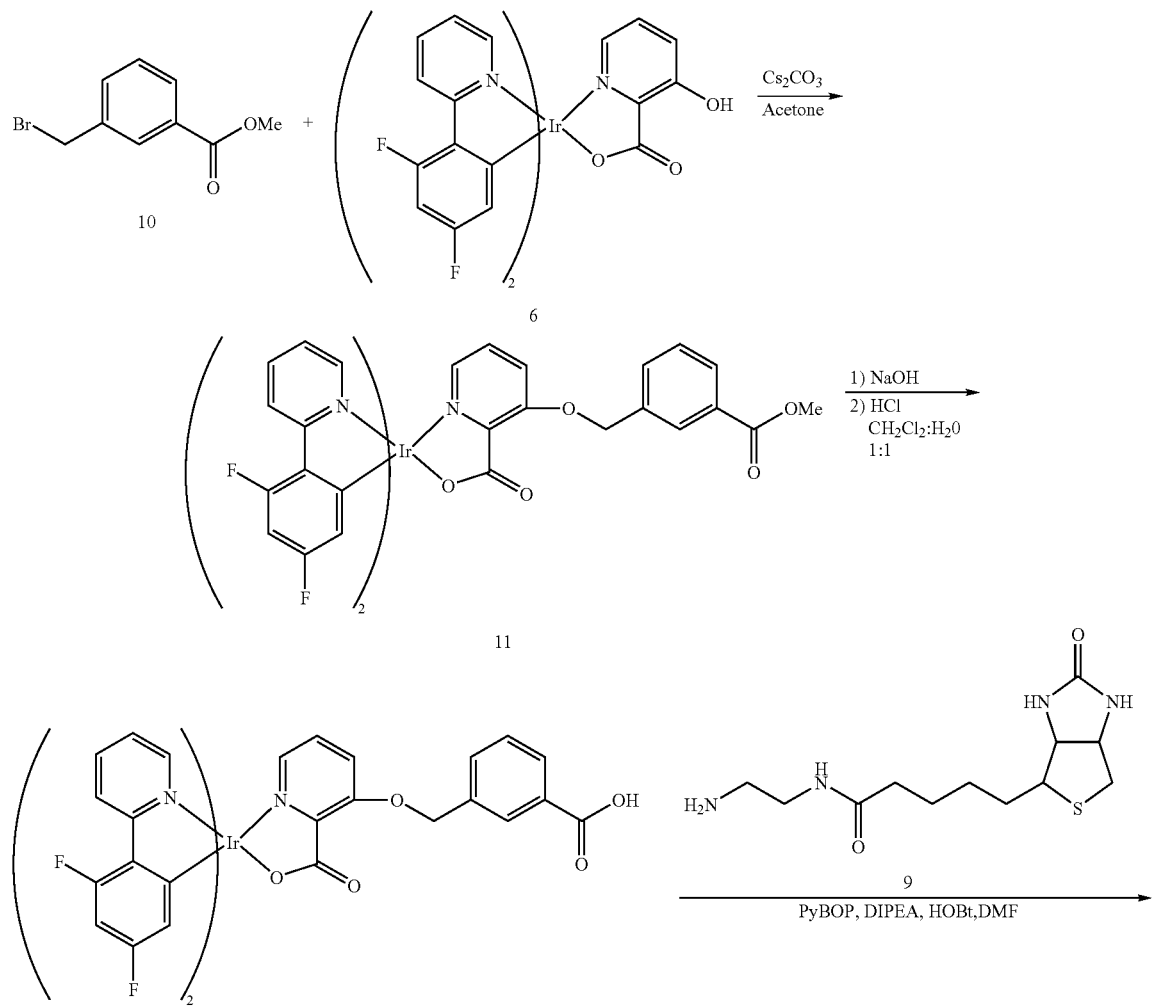

Scheme S3: Synthesis of Probe 2

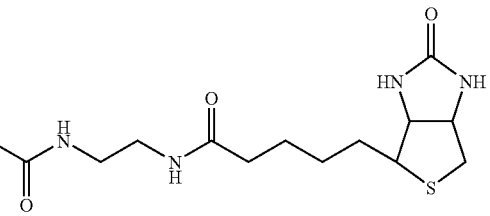

2

Compound 11: A mixture including Compound 10 (110 mg, 0.480 mmol), Flrpic-OH (Compound 6) (352 mg, 0.480 mmol), and $Cs_2CO_3$ (469 mg, 1.44 mmol) was refluxed in acetone for 24 hours. After cooling to room temperature, the solvent was evaporated in vacuum and dissolved in methylene chloride. The organic phase was washed with water and brine and dried over $Na_2SO_4$. The solvent was evaporated to obtain the crude product, which was applied to column chromatography on silica gel, eluting with ethyl acetate and hexane (1:1, v/v) to obtain the desired product (260 mg, yield: 63.1%). The results of the column chromatography for Compound 11 are as follows.

$^1$H NMR (300 MHz, DMSO-$d_6$): δ (ppm) 8.60 (d, 6 Hz, 1H), 8.26 (q, 24 Hz, 2H), 8.15 (s, 1H), 8.05 (q, 15 Hz, 2H), 7.92 (d, 9 Hz, 3H), 7.68 (d, 6 Hz, 1H), 7.50-7.60 (m, 30 Hz, 3H), 7.33 (t, 9 Hz, 2H), 6.78 (q, 12 Hz, 2H), 5.68 (d, 12 Hz, 1H), 5.47 (d, 12 Hz, 1H), 5.37 (s, 2H), 3.87 (s, 3H). $^{13}$C NMR (125 MHz, DMSO-$d_6$): δ (ppm) 169.95, 166.08, 163.53, 162.98, 157.94, 154.51, 153.49, 148.97, 147.99, 140.97, 139.33, 138.34, 137.11, 131.95, 130.18, 129.72, 128.90, 128.48, 127.80, 125.32, 123.96, 123.55, 122.90, 113.64, 69.54, 52.17. MALDI-TOF: calculated for $C_{37}H_{24}F_4IrN_3O_5$ [M]$^+$ 859.13, measured [M]$^+$ 859.41.

Synthesis of Compound 12: To a solution of Compound 11 (260 mg, 0.302 mmol) in $CH_2Cl_2$:$H_2O$ (10 ml:10 ml) was added 1 M NaOH solution. After stirring overnight at room temperature, the reaction mixture was acidified using 1 M HCl solution. The reaction mixture was filtered to obtain a yellow solid (30 mg, yield: 11.7%). The results of the column chromatography for Compound 12 are as follows.

$^1$H NMR (300 MHz, DMSO-$d_6$): δ (ppm) 8.60 (d, 6 Hz, 1H), 8.25 (q, 15 Hz, 2H), 8.04 (m, 12 Hz, 3H), 7.88 (t, 21 Hz, 2H), 7.68 (s, 1H), 7.56 (d, 6 Hz, 1H), 7.47-7.50 (m, 9 Hz, 3H), 7.33 (t, 3 Hz, 2H), 6.78 (q, 12 Hz, 2H), 5.68 (d, 6 Hz, 1H), 5.47 (d, 6 Hz, 1H), 5.35 (s, 2H). $^{13}$C NMR (125 MHz, DMSO-$d_6$): δ (ppm) 169.95, 167.40, 163.62, 158.00, 154.45, 153.43, 148.97, 147.98, 140.91, 139.33, 138.35, 136.64, 131.83, 131.21, 130.14, 128.56, 127.98, 125.35, 123.97, 123.54, 122.80, 122.55, 113.64, 97.50, 69.73. MALDI-TOF: calculated for $C_{36}H_{22}F_4IrN_3O_5$ 845.11, measured [M]$^+$ 845.44.

Synthesis of Compound 2: A mixture of Compound 12 (30 mg, 0.0355 mmol), DIPEA (22.8 mg, 0.177 mmol), PyBOP (55.1 mg, 0.106 mmol), and HOBt (9.59 mg, 0.071 mmol) was stirred in DMF for 1 hour, and biotinylated amine (Compound 9) (11.8 mg, 0.035 mmol) was added thereto. After stirring at room temperature for 12 hours, the solvent was evaporated in high vacuum and dissolved in methylene chloride. The solvent was evaporated to obtain the crude product, which was applied to column chromatography on silica gel, eluting with methylene chloride and methanol (10:1, v/v) to obtain the desired product (10 mg, yield: 25%). The results of the column chromatography for Compound 2 are as follows.

$^1$H NMR (300 MHz, DMSO-$d_6$): δ (ppm) 8.70 (d, 6 Hz, 1H), 8.59 (d, 6 Hz, 1H), 8.43 (s, 1H), 8.26 (q, 24 Hz, 2H), 8.08 (d, 9 Hz, 2H), 8.03 (t, 6 Hz, 2H), 7.93 (d, 9 Hz, 2H), 7.78 (d, 6 Hz, 2H), 7.68 (d, 6 Hz, 2H), 7.57 (t, 9 Hz, 2H), 7.48 (t, 9 Hz, 2H), 7.33 (s, 2H), 6.78 (q, 33 Hz, 2H), 6.34 (d, 15 Hz, 2H), 5.68 (d, 9 Hz, 1H), 5.45 (d, 9 Hz, 1H), 5.34 (s, 2H), 4.27 (d, 6 Hz, 2H), 4.07 (d, 6 Hz, 2H), 3.61 (d, 6 Hz, 2H), 3.14 (d, 9 Hz, 2H), 2.77 (d, 9 Hz, 2H), 2.05 (d, 6 Hz, 2H), 1.48 (m, 6 Hz, 4H), 1.06 (d, 9 Hz, 1H). $^{13}$C NMR (125 MHz, DMSO-$d_6$): δ (ppm) 172.00, 170.10, 166.24, 165.50, 164.50, 161.17, 160.50, 159.00, 158.04, 153.50, 151.50, 148.50, 147.97, 139.41, 138.00, 136.47, 134.64, 130.22, 129.50, 128.38, 126.39, 125.00, 124.00, 116.00, 114.00, 69.89, 61.00, 59.00, 55.74, 52.70, 35.00, 32.00, 28.95, 26.57, 22.06, 18.79, 13.93. MALDI-TOF: calculated for $C_{49}H_{46}F_4IrN_7O_6S$ 1129.2800, measured [M]$^+$ 1129.64. HR-MS: 1129.2798.

Example 4

Photoluminescent (PL) Spectrum

Figure 5:
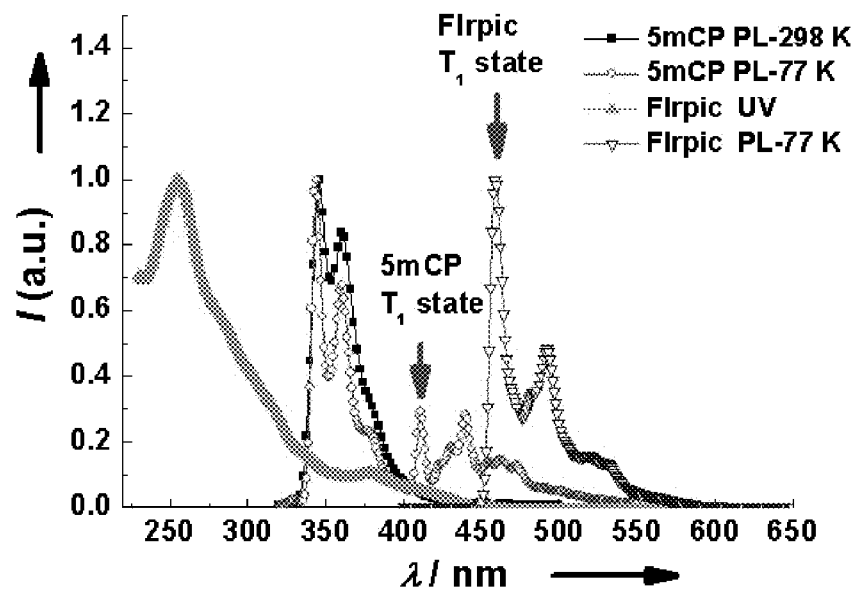
FIG. 5 is a graph illustrating UV spectrum of Flrpic and PL spectrum of 5 mCP and Flrpic in 0.02 M of 2-methyltetrahydrofuran ("2-MeTHF") at 298 K and at 77 K (left)
Figure 6:
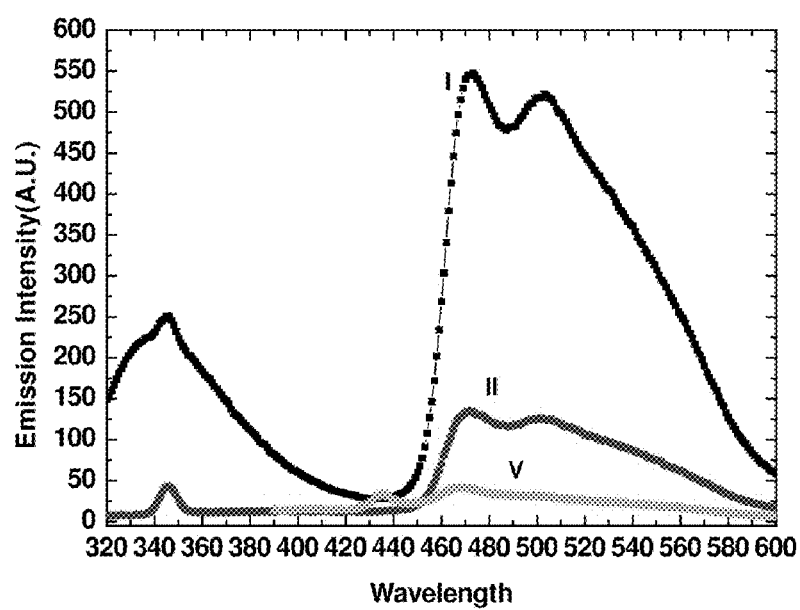
FIG. 6 is a graph illustrating the PL spectra of avidin+Probe 1 (4 eq) (at 310 nm excitation) (I), Probe 1 (at the excitation at 310 nm) (II) and avidin+Probe 2 (4 eq) at 380 nm excitation) (V) in a buffer solution.

The emission intensity of unbound Probe 1 (II) also has high energy transfer efficiency (about 75%. See the energy transfer part). However, the emission intensity of Probe 1-avidin complex is 4-fold higher than that of unbound Probe 1 due to the increased hydrophobicity of the surrounding environment of the bound probe. The results are shown in FIGS. 5 and 6.

Example 5

Luminescence Titration

Aliquots (13.7 μL) of Probes 1 and 2 in DMSO (0.242 mM) were added to a solution of avidin (1.66 μM) in 2 mL of buffer solution at 10 min intervals. The emission intensities of the solutions were measured at 472 nm. The binding of Probes 1 and 2 to avidin was investigated by luminescence titration using the probes as titrants. The results were compared with two series of control titrations in which (i) avidin was absent, and (ii) the avidin solution was saturated with excess free biotin. In addition, in order to prove the energy transfer effect, the emission spectra of Probe 1 in the absence of avidin was obtained by excitation at the energy donor absorption (310 nm) and the energy acceptor absorption (380 nm), respectively. All the titration results are shown in FIG. 7. Each titration result is shown in FIG. 8 to 12.

Figure 8:
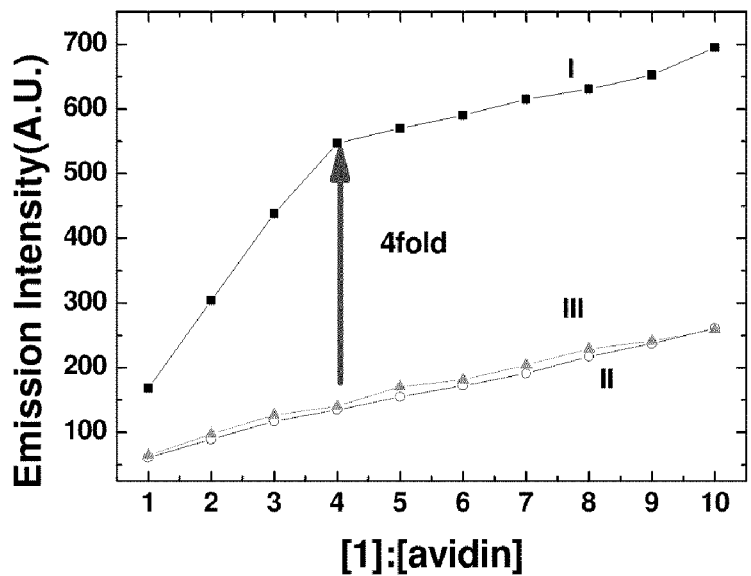
FIG. 8 is a graph illustrating the luminescence intensity change for the titration of avidin with Probe 1 (I), Probe 1 (II), and for the titration of avidin+excess biotin solution with Probe 1 in a buffer solution, at 310 nm excitation (III)

FIG. 8 illustrates shows luminescence intensity changes for Probe 1 with (I) or without avidin (II), when excited at 310 nm. Emission intensity of Probe 1-avidin complex (I) shows about 4-fold increase compared with that of Probe 1 without avidin (II). Curve III shows the titration of avidin+excess biotin with Probe 1.

Figure 9:
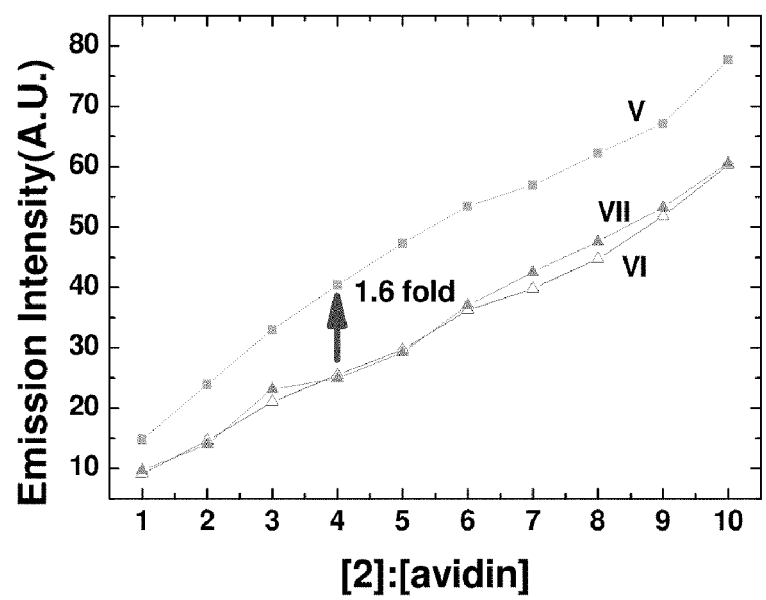
FIG. 9 is a graph illustrating the luminescence intensity change for the titration of Prove 2 (V), Probe 2 in a buffer solution (VI), and the titration of avidin+excess biotin solution with Probe 2 at 380 nm excitation (VII)

FIG. 9 illustrates the luminescence intensity changes for Probe 2 with (V) or without avidin (VI), when excited at 380 nm. Emission intensity of Probe 2-avidin complex (V) shows about 1.6 fold increase compared with that of Probe 2 (VI). Curve VII shows the titration of avidin+excess biotin with Probe 2, when excited at 380 nm.

In order to prove energy transfer efficiency, the Probe 1 in the presence of avidin was excited at 310 nm (I, absorption of the energy donor) and at 380 nm (IV, main absorption of the energy acceptor), respectively, in the presence of avidin. The emission intensity of the Probe 1-avidin complex at the excitation at 310 nm is 4-fold greater than that of the Probe 1-avidin complex at the excitation at 380 nm (FIG. 10).

Figure 11:
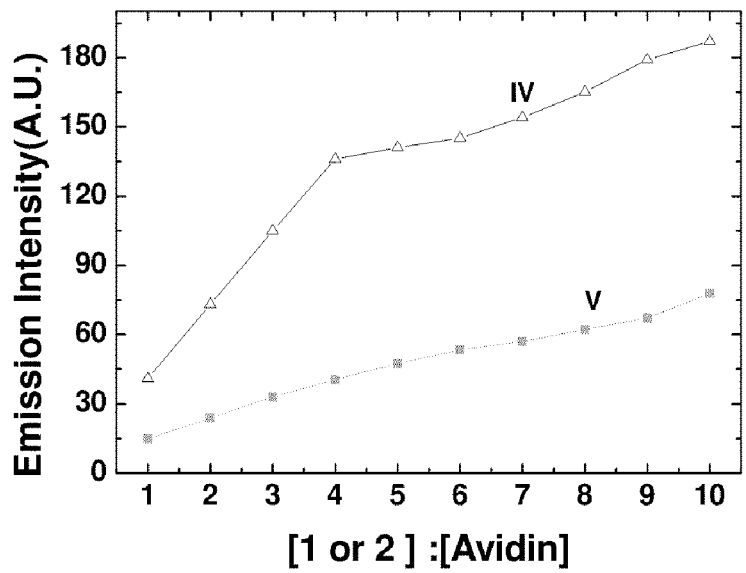
FIG. 11 is a graph illustrating the luminescence intensity change for the titration of avidin with Probe 1 at 380 nm excitation (IV) and avidin with Probe 2 at 380 nm excitation (V)

FIG. 11 illustrates the intrinsic properties of Probes 1 and 2 in the presence of avidin. The emission intensity of Probe 1-avidin at 380 nm excitation (IV) is just only 3.5-fold higher than that of the emission intensity of Probe 2-avidin at 380 nm excitation (V). This is presumably due to the increased hydrophobicity of Probe 1 itself compared with Probe 2, and also due to the increased hydrophobicity associated with binding of Probe 1 to avidin, when compared with the avidin binding with Probe 2.

Figure 10:
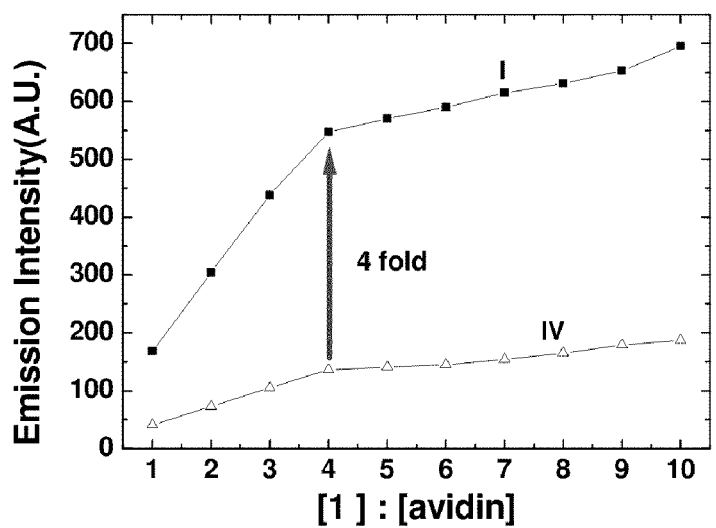
FIG. 10 is a graph illustrating the luminescence intensity change for the titration of avidin with Probe 1 at 310 nm excitation (I) and avidin with Probe 1 at 380 nm excitation (IV)

However, if the hydrophobicity of the donor plays a major role in the increased emission intensity of Probe 1-avidin complex, the emission intensity of Probe 1-avidin at 310 nm excitation (FIG. 10, I) should be similar to that of Probe 1-avidin at 380 nm excitation (FIG. 10, IV). However, as shown in FIG. 10, the emission intensity of Probe 1-avidin at 310 nm excitation (I) is 4-fold higher than that of Probe 1-avidin at 380 nm excitation (IV). This is due to the intramolecular energy transfer from the donor to the acceptor at 310 nm excitation.

As shown in FIGS. 7, 10 and 11, the emission intensity of Probe 1-avidin at 310 nm excitation is 14-fold higher than that of the emission intensity of Probe 2-avidin at 380 nm excitation. The 14-fold increase in the emission intensity of Probe 1-avidin at 310 nm excitation can be divided into two parts; 4-fold increase from the emission intensity of Probe 1-avidin at 380 nm excitation (IV) to that of Probe 1-avidin at 310 nm excitation (emission enhancement by the intramolecular energy transfer), and 3.5-fold increase from the emission intensity of Probe 2-avidin at 380 nm excitation (V) to that of Probe 1-avidin at 380 nm excitation (IV) (emission enhancement by the increased hydrophobicity).

In conclusion, the increase in the emission intensity of Probe 1-avidin complex results from the hydrophobic environment within the binding site of avidin, the increased hydrophobicity of neutral Probe 1 (because of the hydrophobic donor moiety), and the intramolecular energy transfer.

FIG. 12 compares the emission intensity of Probe 1+avidin (I) with that of Compound 8 (which does not have biotin moiety)+avidin (VIII), upon excitation at 310 nm. The emission intensity of Compound 8+avidin (VIII) is similar to that of Probe 1 solution (II), excited at 310 nm (FIG. 12).

Example 6

HABA Assay

The binding of Probes 1 and 2 to avidin was studied using HABA assays, which are based on the competition between biotin and HABA for binding to avidin. Avidin (1.66 µM, 2 mL) and HABA (1 mM, 13.2 µL) were combined in buffer solution and left for 10 min. The binding of HABA to avidin is associated with an absorption feature at about 500 nm. Probe 1 or 2 (0.242 mM, 13.7 µL) was added to the mixture of avidin and HABA. The addition of Probe 1 or 2 into a mixture of avidin and HABA leads to a decrease in the absorbance at 500 nm because of weaker binding of HABA to avidin ($K_d=6\times10^{-6}$ M). The plots of $\Delta A_{500\ nm}$ vs [Probe 1 or 2]: [avidin] indicate that the equivalence points occur at [Probe 1 or 2]:[avidin]=4. Example 7: Determination of $K_d$ The first dissociation constant ($K_d$) between Probe 1 and avidin was determined from the emission titration experiments according to ((a) Wang, Z. X.; Kumar, N. R.; Srivastava, D. K., *Anal. Biochem.* 1992, 206, 376; (b) Lo, K. K. W.; Tsang, K. H. K., *Organometallics* 2004, 23, 3062).

Example 8

Competitive Biotin Assay

The competitive biotin assay is based on the competition between Probe 1 and free biotin for binding to avidin. In the assays, biotin in the range of $10^{-3}$ M to $10^{-11}$ M was added to a mixture of avidin (1.66 µM) and Probe 1 (1.66 µM). After 1 h incubation, emission intensity of Probe 1 gradually decreased according to the concentration of free biotin because the binding of free biotin to avidin ($K_d$=ca. $10^{-15}$ M) is much stronger than that of Probe 1 ($K_d$=ca. $3.8\times10^{-12}$ M). Due to high emission intensity of Probe 1, the linear range for the detection of the free biotin analyte was increased greatly to $10^{-6.5}$ to $10^{-10.5}$ M.

Example 9

Energy Transfer ("ET") Efficiency in 2-MeTHF

Example 9-1

Steady-State PL Method

In the steady-state PL method, ET efficiency was measured from the extent of the luminescence quenching of the donor in the presence of the acceptor, in 2-MeTHF. This was measured from the relative ratio between the integrated area of the singlet and triplet donor peaks in 5 mCP ($IA_{5\ mCP}$) and that of the residual singlet and triplet donor peaks in Probe 1 ($IA_{tripod(1)}$) at 298 K (FIG. 16) and 77 K (FIG. 17). The ET efficiency is $(1-IA_{tripod(1)}/IA_{5\ mCP})\times100(\%)$. This method shows that in the 2-MeTHF solution, the donor emission was almost quenched.

Figure 16:
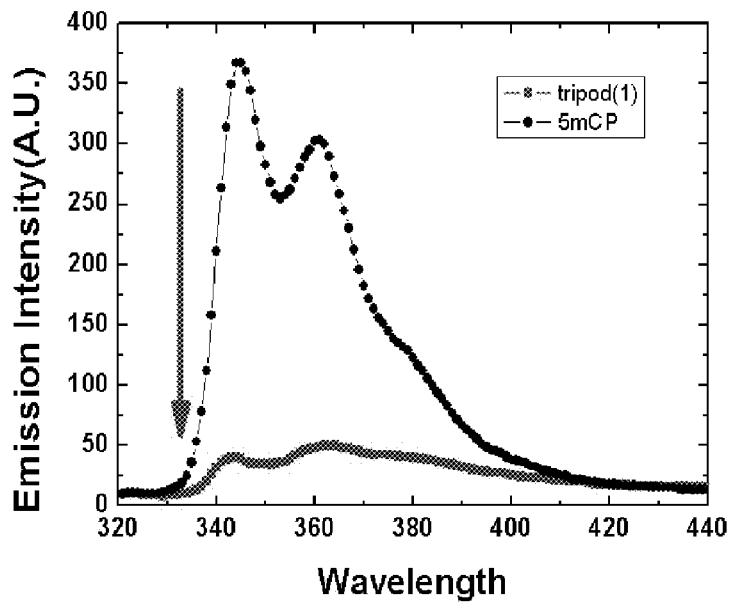
FIG. 16 illustrates a graph illustrating PL spectra of 0.02 mM Probe 1 (tripod 1) and 5 mCP in 2-MeTHF at 298 K (at 310 nm excitation)
Figure 17:
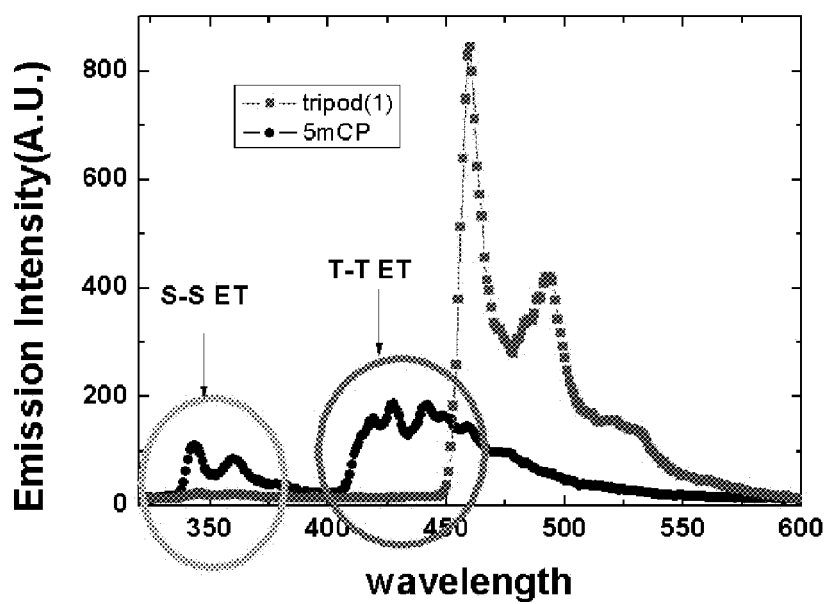
FIG. 17 illustrates a graph illustrating PL spectra of 0.02 mM Probe 1 and 5 mCP in 2-MeTHF at 77 K (at 310 nm excitation)
Figure 18:
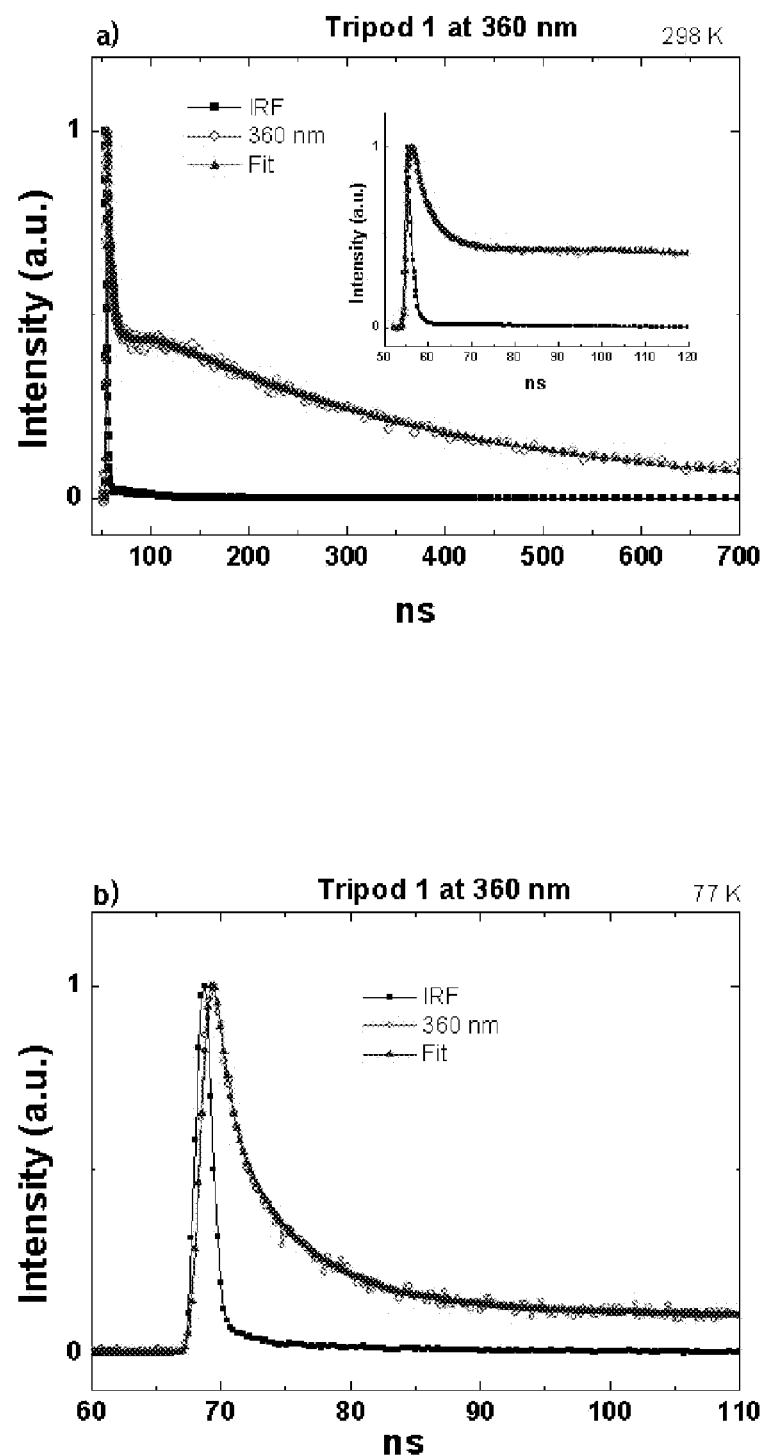
FIGS. 18a-c are graphs illustrating a transient PL spectrum of Probe 1 (0.02 mM) excited at 310 nm, wherein (a) illustrates lifetime of Probe 1 at 298 K 360 nm and an enlarged transient PL spectrum, (b) illustrates lifetime of Probe 1 at 77 K at 360 nm, (c) illustrates lifetime of Probe 1 at 77 K at 411 nm and an enlarged transient PL spectrum. IRF is an instrument response function. Fit is a fitting curve, FIGS. 19A and B illustrates PL spectra of (I) avidin, (II) 5 mCP, (III) avidin+Probe 1, (IV) PL spectra of Probe 1 in a buffer solution excited at 310 nm (19A), and enlarged emission spectrum at 320 to 404 nm (19B).
Figure 18:
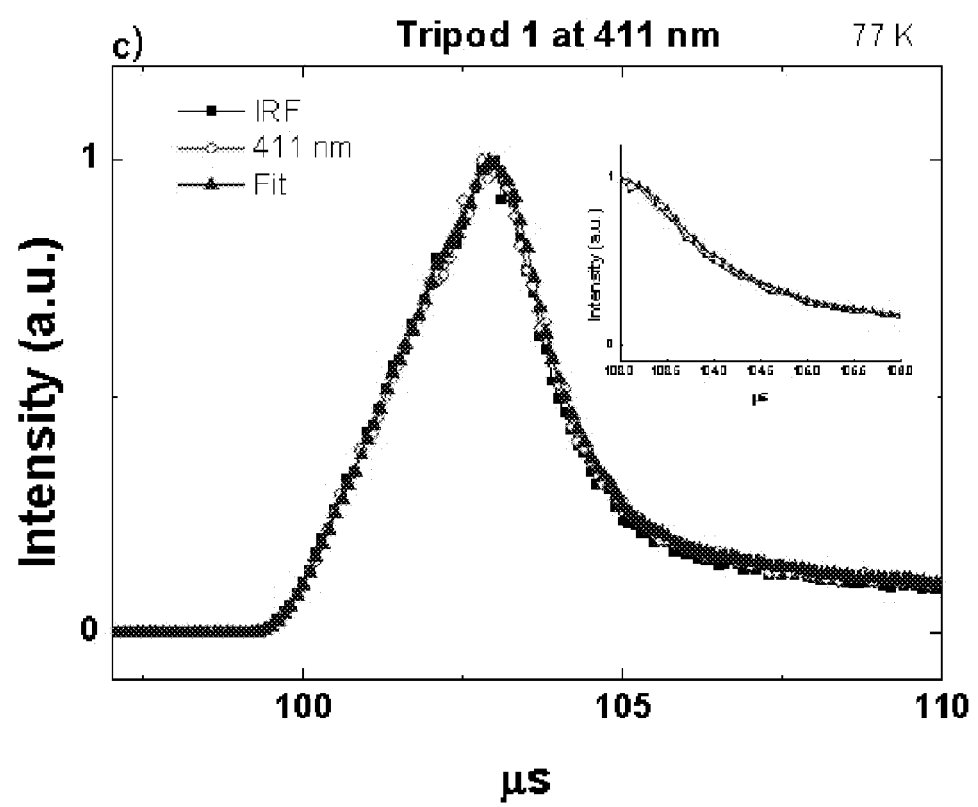

As shown in FIG. 16 and Table 3, the ET efficiency from the donor (5 mCP unit) to the acceptor at 298 K was calculated to be 75% for Probe 1 in 2-MeTHF. At 77 K, singlet-singlet ("S-S") ET (320-404 nm) and triplet-triplet ("T-T") ET efficiency (405-440 nm) were calculated to be 63% and 89%, respectively (FIG. 17 and Table 3). However, this method ignores the detection error caused by the overlap between the emission of the acceptor moiety and the triplet emission of the donor moiety above 450 nm. The expected error in the steady-state PL method can be overcome by measuring lifetimes more precisely.

Example 9-2

Transient PL Method

ET efficiency was also measured using transient PL data (Table 3) from the following equation, assuming that the ET time constants were considerably more rapid than the luminescence decay from the residual unquenched donor peak of Probe 1:

$$ET\ efficiency(\%) = (1 - \tau_{D-A}/\tau_D) \times 100$$

In the equation, $\tau_{D-A}$ is lifetime of donor-acceptor conjugate (Probe 1), and $\tau_D$ is lifetime of donor (5 mCP).

The transient PL spectra of Probe 1 exhibited almost biexponential curve while that of 5 mCP[3] was monoexponential at 360 nm (Kwon, T.-H.; Kim, M. K.; Kwon, J.; Lee, C. L.; Kim, J. J.; Park, S. J.; Shin, D. Y.; Hong, J. I., *Chem. Mater.* 2007, 19, 3673). The main component of the lifetime of the donor moiety of Probe 1 was dramatically shortened (0.50 ns at 298 K) as compared to that of 5 mCP (6.6 ns at 298 K). The longer lifetime component for Probe 1 (5.2 ns at 298 K) is similar to that of 5 mCP. This results presumably from the residual unquenched donor peak of Probe 1 or from the conformational heterogeneity that prevents energy transfer. The decrease in the lifetime of the donor peak in Probe 1 at 360 nm indicates the intramolecular ET from the donor to the acceptor. The S-S ET efficiency obtained from the above equation is calculated to be 92% at 298 K.

The lifetime of the donor peaks in Probe 1 at 360 and 411 nm was also measured at 77 K to calculate the ET efficiency precisely. The lifetime of the donor peak at 360 nm in Probe 1 was also dramatically shortened to 0.90 ns as compared to that of 5 mCP. (8.2 ns at 77 K). The longer lifetime at 360 nm (4.7 ns) may also be derived from the unquenched donor peak or from the conformational heterogeneity. The S-S ET efficiency measured by the transient PL method was calculated to be 90%, which is similar to that measured by the transient PL method at 298 K. The lifetime of the donor peak at 411 nm in Probe 1 was also dramatically shortened to 0.11 μs as compared to that of 5 mCP (7.0 sec). Thus, T-T ET efficiency of Probe 1 was calculated to be more than 99%.

TABLE 2

Lifetime of the donor peak in Probe 1 at 298 K and 77 K

|  | $T_{360\ nm}$ (ns)[a] | $T_{360\ nm}$ (ns)[b] | $T_{411\ nm}$ (s)[c] |
|---|---|---|---|
| 5mCP[d] | 6.6 ns | 8.2 ns | 7.0 s |
| Probe 1 | 0.50 ns (64%) | 0.90 ns (66%) | 0.11 μs (100%) |
|  | 5.2 ns (24%) | 4.7 ns (31%) |  |

[a] lifetime of the donor peak (360 nm) after excitation at 310 nm in 0.02 mM 2-Me THF solution at 298 K.
[b] data obtained at 77 K.
[c] lifetime of the donor peak (411 nm) when excited at 310 nm in 0.02 mM 2-Me THF solution at 77 K. Lifetime of 5mCP was measured in seconds.
[d] these data are derived from a method disclosed in Kwon, T. H.; Kim, M. K.; Kwon, J.; Lee, C. L.; Kim, J. J.; Park, S. J.; Shin, D. Y.; Hong, J. I., *Chem. Mater.* 2007, 19, 3673.

TABLE 3

Energy Transfer Efficiency of Probe 1

|  | Transient PL ET(%) | | | Steady-state PL ET(%) | | |
|---|---|---|---|---|---|---|
|  | 298 K $\Phi_{360\ nm}$[a] | 77 K $\Phi_{360\ nm}$[b] | 77 K $\Phi_{411\ nm}$[c] | 298 K $\Phi_s$[d] | 77 K $\Phi_s$[e] | 77 K $\Phi_t$[f] |
| Probe 1 | 92% | 90% | >99% | 75% | 63% | 89% |

[a] Energy transfer (%) = $(1 - T_{probe(1)\ 360\ nm}/T_{5mCP\ 360\ nm}) \times 100$ at 298 K.
[b] $T_{probe(1)\ 360\ nm}$ at 77 K.
[c] $T_{probe(1)\ 411\ nm}$ at 77 K.
[d] The ET efficiency was measured from the relative ratio between integrated area of the singlet and triplet donor peak in 5mCP ($IA_{5mCP}$) and that of the residual singlet and triplet donor peak in Probe 1. Energy transfer (%) = $(1 - IA_{probe(1)}/IA_{5mcp}) \times 100$.
[e] The S-S ET efficiency at 77 K. The ET was measured from the relative ratio between the integral area of the singlet donor peak (320 to 404 nm) in 5mCP ($IA_{5mCP}$) and that of the residual singlet donor peak in the Probe 1.
[f] T-T ET efficiency at 77 K. The ET efficiency was measured from the relative ratio between the integrated area of the triplet donor peak (405 to 440 nm) in 5mCP ($IA_{5mCP}$) and that of the residual triplet donor peak in Probe 1.

Example 10

Energy Transfer Efficiency in Buffer Solution

Figure 19A:
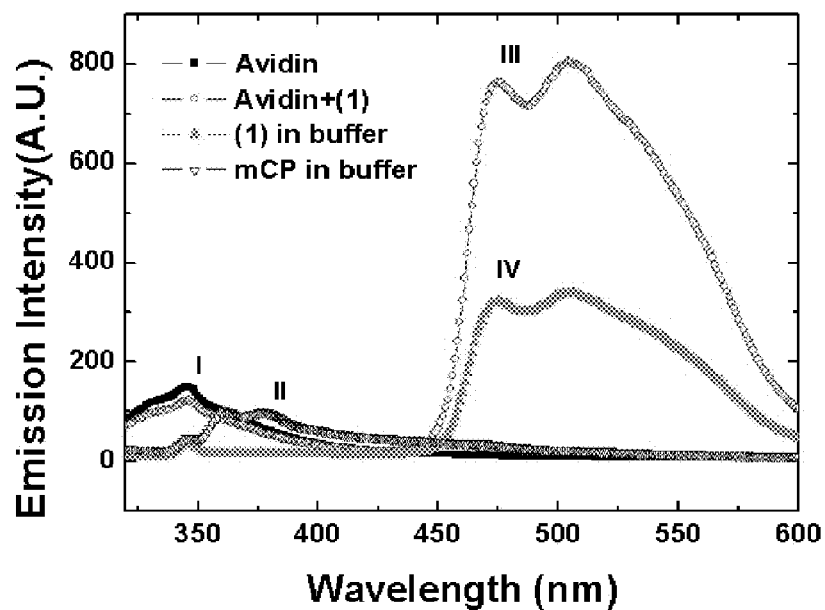
Figure 19B:
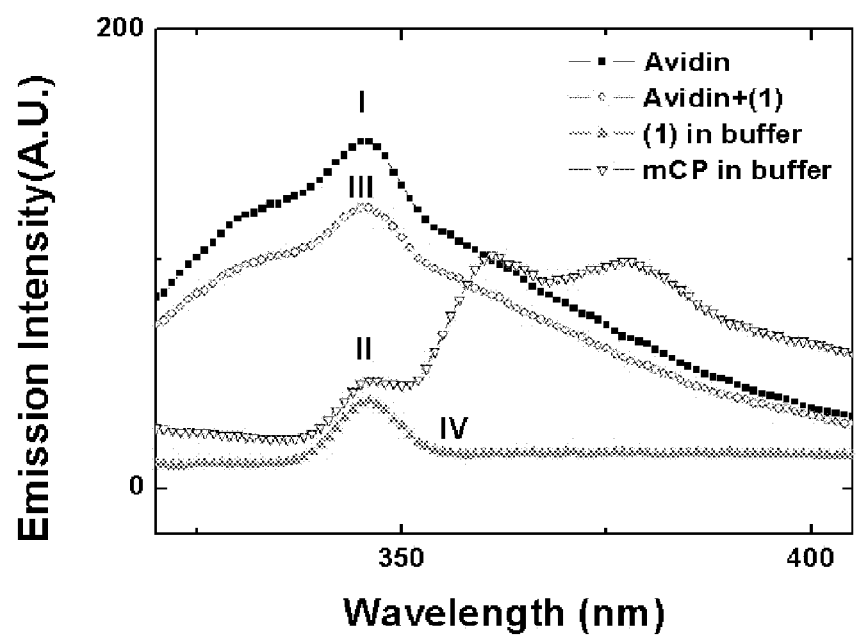

In buffer solution, the residual peak intensity of the donor part in Probe 1 (330 to 360 nm region) when excited at 310 nm (FIGS. 19A and B, IV) is relatively small as compared with that of only the donor (5 mCP) without an acceptor (II). The ET efficiency of Probe 1 (IV) was calculated to be 74%. In contrast, in the presence of avidin solution, the ET efficiency can't be exactly measured because donor emission (III) in the range of 320 to 420 nm is overlapped with avidin emission (I) when excited at 310 nm. However, as shown in FIGS. 19A and B, the emission structure and intensity of Probe 1+avidin in the range of 320 to 420 nm (III) are very similar to those of only avidin in the same spectral range (I). This suggests that the residual peak of Probe 1+avidin in the range of 320 to 420 nm (III) is derived from the avidin emission peak. Therefore, the ET efficiency in Probe 1+avidin was calculated to be more than 74%.

TABLE 4

Energy Transfer Efficiency of Probe 1 in Buffer solution*

|  | without avidin | with avidin |
|---|---|---|
| Probe 1 | 74% | >74% |

*The ET efficiency was measured from the relative ratio between integrated area of the donor peak (320 to 440 nm) in 5mCP ($IA_{5mCP}$) and that of the residual donor peak in Probe 1 (320 to 440 nm). Energy transfer efficiency (%) = $(1 - IA_{probe(1)}/IA_{5mcp}) \times 100(\%)$.

As described above, a luminescence biotin-transition metal complex conjugate using a transition metal probe provides a phosphorescence detection system overcoming problems of sensitivities of existing biotin-avidin assays. The inventive luminescence biotin-transition metal complex conjugate offers remarkable sensitivity over traditional transition metal based protein probes due to the intramolecular energy transfer and increased hydrophobicity associated with the avidin binding site and neutral probe 1.

While disclosed embodiments have been shown and described with reference to exemplary embodiments thereof, it will be understood by those of ordinary skill in the art that various changes in form and details may be made therein without departing from the spirit and scope of the present invention as defined by the following claims.

In addition, many modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguished one element from another. Furthermore, the use of the terms a, an, etc. do not denote a limitation of quantity, but rather denote the presence of at least one of the referenced item.

What is claimed is:

1. A luminescence biotin-transition metal complex conjugate comprising an energy acceptor and biotin, represented by Formula 1 or Formula 2 below:

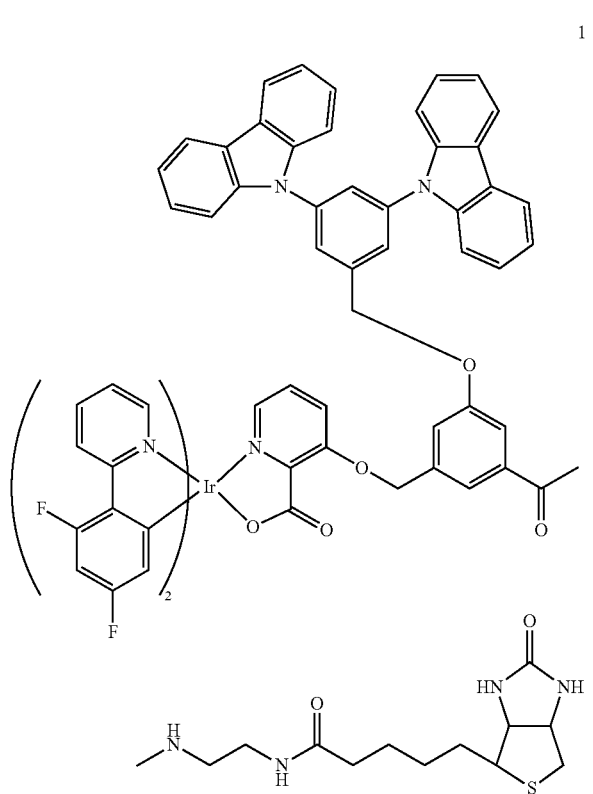

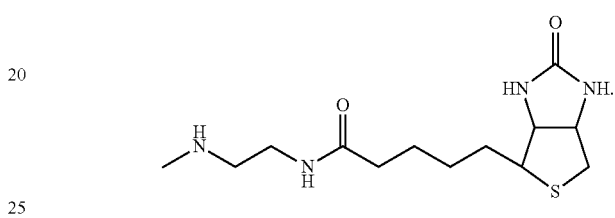

2. The luminescence biotin-transition metal complex conjugate of claim 1, wherein the conjugate is represented by Formula 2.

3. The luminescence biotin-transition metal complex conjugate of claim 1, wherein the conjugate is represented by Formula 1.

* * * * *